United States Patent
Gerspacher et al.

Patent Number: 5,248,693
Date of Patent: Sep. 28, 1993

[54] ACETYLENE COMPOUNDS AND PHARMACEUTICAL COMPOSITIONS AND METHODS OF USING THE SAME

[75] Inventors: Marc Gerspacher, Aeschi; Alfred Sallmann, Bottmingen; Rolf Schurter, Binningen, all of Switzerland

[73] Assignee: Ciba-Geigy Corporation, Ardsley, N.Y.

[21] Appl. No.: 964,184

[22] Filed: Oct. 21, 1992

[30] Foreign Application Priority Data

Oct. 25, 1991 [CH] Switzerland .......... 3135/91

[51] Int. Cl.$^5$ .............. A61K 31/405; C07D 209/08
[52] U.S. Cl. .......................... 514/415; 548/510
[58] Field of Search ............ 514/415; 548/511, 510

[56] References Cited

U.S. PATENT DOCUMENTS

| | | |
|---|---|---|
| 4,859,692 | 8/1989 | Bernstein et al. |
| 4,918,094 | 4/1990 | Bernstein et al. |
| 5,096,917 | 3/1992 | Sallmann et al. |

FOREIGN PATENT DOCUMENTS

| | | |
|---|---|---|
| 199543 | 10/1986 | European Pat. Off. |
| 0220066 | 4/1987 | European Pat. Off. |
| 0227241 | 7/1987 | European Pat. Off. |
| 0337766 | 10/1989 | European Pat. Off. |
| 0455596 | 11/1991 | European Pat. Off. |

Primary Examiner—Joseph Paul Brust
Assistant Examiner—Jacqueline Haley
Attorney, Agent, or Firm—Irving M. Fishman; Karen G. Kaiser

[57] ABSTRACT

The invention relates to compounds of formula I

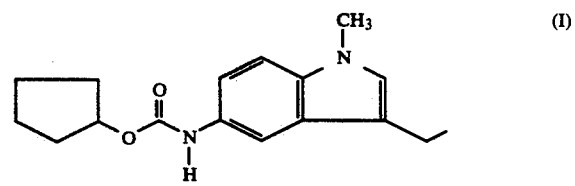

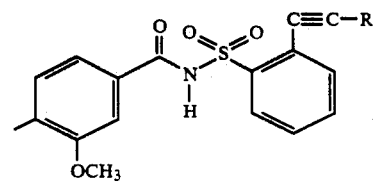

wherein
R is hydrogen or $C_1$-$C_7$alkyl, or wherein R is the structural element-alk-$R_1$ in which alk is $C_1$-$C_7$alkylene, $C_2$-$C_7$alkylidene or $C_3$-$C_6$cycloalkylidene and $R_1$ is hydroxy, $C_1$-$C_7$alkoxy, phenyl-$C_1$-$C_7$alkoxy or $C_2$-$C_7$alkanoyloxy;

in free form or in the form of a salt; processes for their preparation, their use, and also pharmaceutical compositions comprising a compound of formula I in free form or in the form of a pharmaceutically acceptable salt.

16 Claims, No Drawings

ACETYLENE COMPOUNDS AND PHARMACEUTICAL COMPOSITIONS AND METHODS OF USING THE SAME

The invention relates to compounds of formula I,

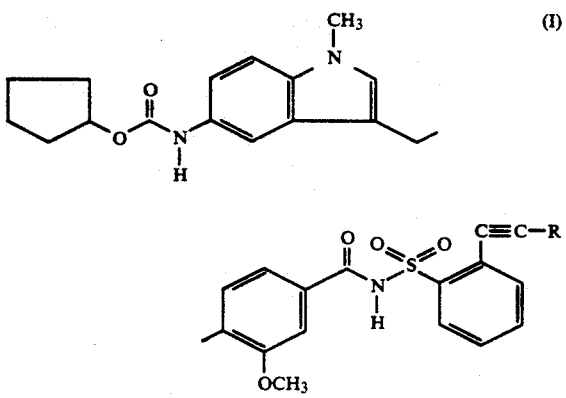

wherein
R is hydrogen or $C_1$-$C_7$alkyl, or wherein R is the structural element-alk-$R_1$ in which alk is $C_1$-$C_7$alkylene, $C_2$-$C_7$alkylidene or $C_3$-$C_6$cycloalkylidene and $R_1$ is hydroxy, $C_1$-$C_7$alkoxy, phenyl-$C_1$-$C_7$alkoxy or $C_2$-$C_7$alkanoyloxy;

in free form or in the form of a salt; processes for their preparation, their use, and also pharmaceutical compositions comprising a compound of formula I in free form or in the form of a pharmaceutically acceptable salt.

Salts of compounds I are especially pharmaceutically acceptable salts, for example acid addition salts, that are formed, for example, with strong inorganic acids, such as mineral acids, e.g. sulfuric acid, a phosphoric acid or a hydrohalic acid, with strong organic carboxylic acids, such as lower alkanecarboxylic acids, e.g. acetic acid, such as saturated or unsaturated dicarboxylic acids, e.g. malonic, maleic or fumaric acid, or such as hydroxycarboxylic acids, e.g. tartaric or citric acid, or with sulfonic acids, such as lower alkanesulfonic acids or unsubstituted or substituted benzenesulfonic acids, e.g. methane-or p-toluene-sulfonic acid, or salts with bases, such as corresponding alkali metal or alkaline earth metal salts, e.g. sodium, potassium or magnesium salts, pharmaceutically acceptable transition metal salts, such as zinc or copper salts, or salts with ammonia or organic amines, such as cyclic amines, such as mono-, di- or tri-lower alkylamines, such as hydroxy-lower alkylamines, e.g. mono-, di- or tri-hydroxy-lower alkylamines, hydroxy-lower alkyl-lower alkylamines or polyhydroxy-lower alkylamines. Cyclic amines are e.g. morpholine, thiomorpholine, piperidine or pyrrolidine. Suitable mono-lower alkylamines are, for example, ethyl- and t-butyl-amine, suitable di-lower alkylamines are, for example, diethyl- and diisopropyl-amine and suitable tri-lower alkylamines are, for example, trimethyl- and triethyl-amine. Corresponding hydroxy-lower alkylamines are e.g. mono-, di- and tri-ethanolamine; hydroxy-lower alkyl-lower alkylamines are e.g. N,N-dimethylamino-and N,N-diethylamino-ethanol; a suitable polyhydroxy-lower alkylamine is e.g. glucosamine. Salts that are not suitable for pharmaceutical purposes are also included, since they can be used, for example, for the isolation and purification of free compounds I and pharmaceutically acceptable salts thereof.

Unless defined otherwise, radicals and compounds designated hereinbefore and hereinafter as "lower" are to be understood as being those having up to and including 7, especially up to and including 4, carbon atoms.

$C_1$-$C_7$Alkyl is e.g. methyl, ethyl, n-propyl, isopropyl, n-butyl, isobutyl, sec-butyl, tertbutyl or a corresponding pentyl, hexyl or heptyl radical. $C_1$-$C_5$alkyl is preferred.

$C_1$-$C_7$Alkylene is straight-chain or branched and is especially methylene, ethylene, 1,2-or 1,3-propylene, 1,2-, 1,3-, 1,4- or 2,3-butylene, 2-methyl-1,2- or -1,3-propylene or 2,2-dimethyl-1,2- or -1,3-propylene. $C_1$-$C_5$Alkylene is preferred.

$C_2$-$C_7$Alkylidene is e.g. ethylidene, 1,1- or 2,2-propylidene, 1,1-or 2,2-butylidene, 1,1- or 2,2-or 3,3-pentylidene, 2-methyl-1,1- or -3,3-butylidene, 2-methyl-1,1- or -3,3-pentylidene.

$C_3$-$C_6$Cycloalkylidene is e.g. cyclopropylidene, cyclobutylidene, cyclopentylidene or cyclohexylidene. Cyclopentylidene and cyclohexylidene are preferred.

$C_1$-$C_7$Alkoxy is e.g. methoxy, ethoxy, n-propoxy, isopropoxy, n-butoxy, isobutoxy, sec-butoxy, tertbutoxy or corresponding pentyloxy, hexyloxy or heptyloxy. $C_1$-$C_4$Alkoxy is preferred.

Phenyl-$C_1$-$C_7$alkoxy is especially phenyl-$C_1$-$C_4$alkoxy and is preferably benzyloxy or 1- or 2-phenethoxy.

$C_2$-$C_7$Alkanoyloxy is e.g. acetyl-, propionyl-, butyryl-, isobutyryl- or pivaloyl-oxy. $C_2$-$C_5$-Alkanoyloxy is preferred.

The compounds I and their pharmaceutically acceptable salts have, for example, valuable pharmacological properties, especially a pronounced antagonistic action against leucotrienes.

For example, in vitro in a concentration range of from approximately 0.001 to approximately 1 $\mu$mol/l they inhibit the contraction of smooth muscle induced by leucotriene $D_4$ ($LTD_4$). This action, called $LTD_4$-antagonism, can be verified by experiment, e.g. by triggering contractions with synthetic leucotriene $D_4$ (in the form of a potassium salt), and recording those contractions isotonically, in segments that have been removed from the ileum of a 300–400 g guinea pig and incubated in an organ bath in Tyrode's solution at 38° C. with gassing with a mixture of 95% oxygen and 5% carbon dioxide at a load of 1 g. The extent to which the test compound inhibits the contractions is ascertained in the form of the $IC_{50}$ after a preincubation of 2 minutes, the $IC_{50}$ indicating that concentration at which the test contractions are reduced by 50%.

The compounds I and their pharmaceutically acceptable salts are also extremely effective in vivo. In the standard bronchoconstriction test on a guinea pig, for example, a clear $LTD_4$-antagonistic effect is observed on administration of an aerosol solution comprising from approximately 0.00001 to approximately 1% by weight of test compound. In that test model male guinea pigs weighing 400 to 700 g are anaesthetised intraperitoneally with 1.4 g/kg of urethane and a polyethylene cannula is inserted into the jugular vein. A second polyethylene cannula is inserted into the trachea. Using a cannula inserted into the oesophagus, with the cannula connected to a Statham pressure transducer, the pressure in the oesophagus is recorded. The animal is placed in a plexiglass chamber, which can be closed in an airtight manner and is connected to a Fleisch tube No. 000 and a validyne transducer MP 45-1. This arrangement is used to measure the flow. After surgical preparation of the test animals a certain amount of time is allowed to pass so that the pulmonary functions can stabilise. The test substance is then administered in accordance with the following protocol. The test animals are exposed for one minute to a 1% (weight/volume) aerosol solution of the test compound or to distilled water (for control purposes). For all test compounds that are administered by inhalation, a Monaghan ultrasound spray apparatus (model 670) with a particle size ranging from 1 to 8 microns, the major portion being 3 microns, is used. Aqueous solutions and DMSO/water mixtures are each freshly prepared and introduced using an on-stream drug vial into the chamber of the spray apparatus. The spray mist produced is administered to the test animals through a glass chamber of 65 ml capacity which is connected by a cannula to the trachea. At the end of the treatment time, $LTD_4$ (0.3 μg/ml) is administered with a second Monaghan ultrasound spray apparatus (model 670) and through an identical glass chamber for a period of 2 minutes. The decrease in compliance is read in the 3rd minute after $LTD_4$ administration: the mean value of three animals is compared with the mean value of three control animals, and the percentage inhibition of the compliance (% inhibition) is calculated in accordance with the following formula:

$$\% \text{ inhibition} = 100 - \frac{(100 - \text{compliance composition}) \cdot 100}{(100 - \text{compliance control})}$$

If different concentrations of active ingredient are being studied, the percentage inhibition is recorded for each concentration and the "log concentration" is plotted on the abscissa against "percentage inhibition" on the ordinate. The $IC_{50}$ is then determined by linear regression analysis.

The compounds I furthermore exhibit excellent activity in the in vivo test described by W. H. Anderson et al., Br. J. Pharmacol. 78 (1983) 67, in which a leucotriene-dependent bronchospasm is induced by the antigen ovalbumin in anaesthetized, artificially respirated guinea pigs.

The compounds I and their pharmaceutically acceptable salts furthermore have the specific and therapeutically very significant advantage of an unexpectedly high activity and a relatively long duration of action.

The compounds I and their pharmaceutically acceptable salts may therefore be used therapeutically in all cases in which the action of leucotriences leads to pathological conditions, reducing or eliminating that action. Leucotrienes play an important role inter alia in the development of allergic and inflammatory processes. Consequently, the compounds I and their pharmaceutically acceptable salts may be used, for example, as active ingredients in anti-allergic agents that are used, e.g., for the treatment of allergic conditions and disorders, such as, especially, asthma, and also hay fever and obstructive lung disorders. The compounds of formula I and their pharmaceutically acceptable salts can also be used, for example, for the treatment of inflammatory disorders of the lungs and other organs, such as cystic fibrosis and adult respiratory distress syndrome, and furthermore also e.g. for Colitis ulcerosa and Crohn's disease, septic shock and inflammatory disorders of the eye.

One object of the invention is thus the use of compounds I and their pharmaceutically acceptable salts for the preparation of appropriate medicaments. Commercial manufacture of the active ingredients is also included.

Especially preferred are compounds of formula I wherein R is hydrogen or $C_1$–$C_5$alkyl, or wherein R is the structural element-alk-$R_1$ in which alk is $C_1$–$C_5$alkylene, $C_2$–$C_7$alkylidene or $C_3$–$C_6$cycloalkylidene and $R_1$ is hydroxy, $C_1$–$C_4$alkoxy, phenyl-$C_1$–$C_4$alkoxy or $C_2$–$C_7$alkanoyloxy; in free form or in the form of a salt.

Especially preferred are compounds of formula I wherein R is hydrogen or $C_1$–$C_4$alkyl, or wherein R is the structural element-alk-$R_1$ in which alk is $C_1$–$C_4$alkylene or $C_2$–$C_5$-alkylidene and $R_1$ is hydroxy, $C_1$–$C_4$alkoxy or $C_2$–$C_5$alkanoyloxy; in free form or in the form of a salt.

Especially preferred are compounds of formula I wherein R is hydrogen or $C_1$–$C_3$alkyl, such as n-propyl; in free form or in the form of a salt.

Especially preferred are compounds of formula I wherein R is the structural element -alk-$R_1$ in which alk is $C_1$–$C_4$alkylene, such as 1,3-propylene, or $C_2$–$C_5$alkylidene, such as ethylidene or 2,2-propylidene, and $R_1$ is hydroxy; in free form or in the form of a salt.

Especially preferred are compounds of formula I wherein R is the structural element -alk-$R_1$ in which alk is 1,3-propylene, ethylidene or 2,2-propylidene and $R_1$ is hydroxy; in free form or in the form of a salt.

Specifically preferred within the scope of the invention are the compounds of formula I and their salts mentioned in the Examples.

The present invention relates also to processes for the preparation of a compound of formula I, or a salt thereof, which comprise, for example, a) reacting a compound of formula IIa

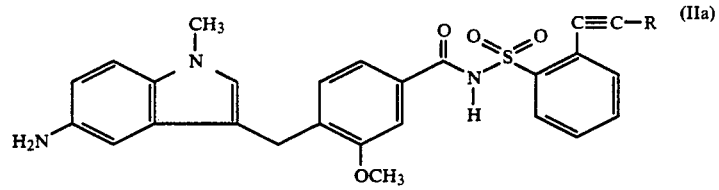

or a salt thereof, with a compound of formula IIb

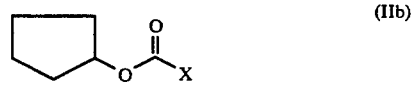

wherein X is a nucleofugal leaving group, with removal of an H-X compound; or b) in a compound of formula III

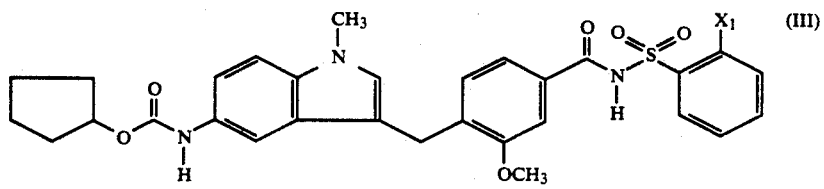

wherein $X_1$ is a group that can be converted into the radical —C≡C—R, or in a salt thereof, converting $X_1$ into the radical —C≡C—R; or c) reacting a compound of formula IVa

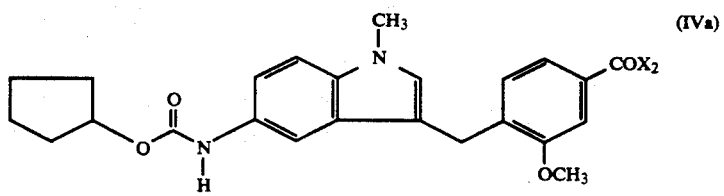

wherein $X_2$ is

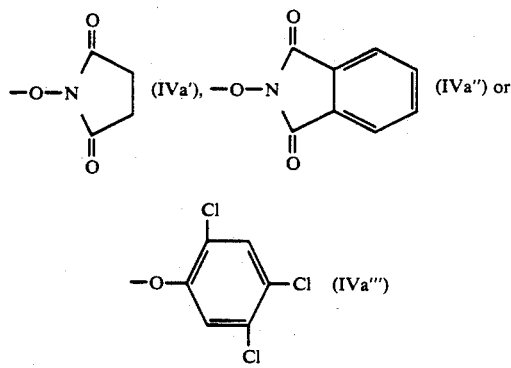

with a compound of formula IVb

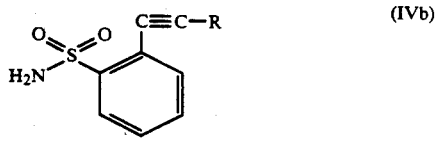

or with a salt thereof;

and, if desired, in each case converting a compound of formula I into a different compound of formula I and/or converting a free compound I obtainable in accordance with the process into a salt or converting a salt obtainable in accordance with the process of a compound I into the free compound I or into a different salt and/or isolating the compound of formula I or a salt thereof.

The reactions described hereinbefore and hereinafter are carried out in the absence or customarily in the presence of a suitable solvent or diluent or a mixture thereof, as required with cooling, at room temperature or with heating, for example in a temperature range of approximately from −80° C. to the boiling temperature of the reaction medium, preferably from approximately −20° to approximately +150° C., and, if necessary, in a closed vessel, under pressure, in an inert gas atmosphere and/or under anhydrous conditions. Especially advantageous reaction conditions are disclosed in the Examples.

The starting materials mentioned hereinbefore and hereinafter that are used for the preparation of compounds I and their salts are known or can be prepared according to methods known per se, for example in accordance with the procedures described hereinafter.

The afore-mentioned information concerning salts of compounds I applies analogously to salts of starting materials mentioned hereinbefore and hereinafter.

Nucleofugal leaving groups X are, for example, esterified hydroxy or cyclopentyloxycarbonyloxy.

A group $X_1$ that can be converted into the radical —C≡C—R is especially halogen; $X_1$ also represents, for the preparation of compounds I wherein R is hydrogen, a group of formula —C≡C—Z wherein Z is e.g. a silyl radical.

Variant a): Esterified hydroxy X is especially hydroxy esterified by a mineral acid, especially halogen. X is preferably halogen, such as chlorine, bromine or iodine. An especially preferred leaving group X is cyclopentyloxycarbonyloxy.

The reaction of a compound IIa or a salt thereof with a compound IIb is carried out in customary manner, e.g. with cooling, at room temperature or with heating, where appropriate in the presence of an inert solvent or diluent or a mixture thereof, where appropriate in the presence of a basic agent and/or under an inert gas.

Suitable inert solvents or diluents are, for example, cyclic ethers, aromatic hydrocarbons, N,N-di-lower alkyl-lower alkanoic acid amides, phosphoric acid lower alkylamides, di-lower alkyl sulfoxides, cyclic amines and, especially, unsubstituted or halogenated hydrocarbons, for example tetrahydrofuran, dioxane, benzene, toluene, xylene, N,N-di-methylformamide, hexamethylphosphoric acid triamide, dimethyl sulfoxide, pyridine, N-methylmorpholine and, especially, hexane and di- and tri-chloromethane.

Suitable basic agents are e.g. alkali metal or alkaline earth metal hydroxides, hydrides, amides, lower alkanolates, carbonates, di-lower alkylamides or lower alkylsilylamides; also lower alkylamines, unsubstituted or N-lower alkylated cycloalkylamines, basic heterocycles, ammonium hydroxides and carbocyclic amines. Sodium hydroxide, hydride, amide and methanolate, potassium tert-butanolate and carbonate, lithium diisopropylamide, potassium bis(trimethylsilyl)amide, calcium hydride, triethylamine, cyclohexylamine, N-cyclohexyl-N,N-dimethylamine, pyridine, N-methylmorpholine, benzyltrimethylammonium hydroxide and 1,8-diazabicyclo[5.4.0]undec-7-ene (DBU) may be mentioned by way of example.

In a preferred form of Variant a), a compound IIa is reacted at room temperature, under nitrogen or argon, in a halogenated hydrocarbon, preferably in dichloromethane, and in the presence of a basic heterocycle, preferably in the presence of N-methylmorpholine, with a compound IIb wherein X is halogen, preferably chlorine.

In an especially preferred form of that Variant, the compound of formula IIa concerned is reacted with the compound of formula IIc

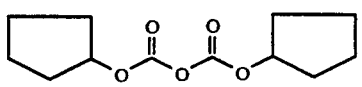
(IIc)

(dicyclopentyl dicarbonate). Advantageous results, for example higher yields, are achieved with that form of process as compared with the use of other compounds of formula IIb, for example those in which X is halogen, such as chlorine.

The compound of formula IIc is novel and, like the process for it preparation and also its use, for example as an acylation agent for the introduction of cyclopentyloxycarbonyl, also forms part of the present invention.

Compounds IIa and salts thereof may be prepared, for example, as follows: The starting material used is, e.g., an ester of the 5-nitroindole compound of formula IId

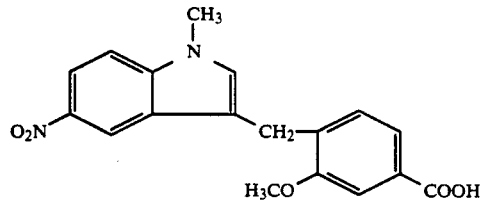
(IId)

(see EP 199 543); the ester is hydrolysed to the free carboxylic acid of formula IId, for example in the presence of a base or acid, the carboxy group is activated and the resulting compound is reacted analogously to Variant c) with a compound of formula IVb (see above), or with a salt thereof, to form a compound of formula IIe

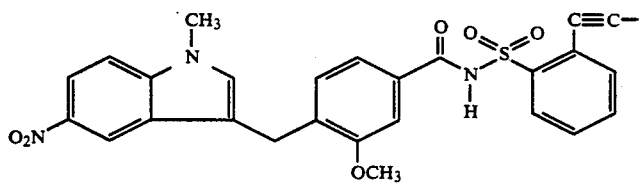
(IIe)

This is reduced to the corresponding amino compound of formula IIa using, for example, a tin(II) halide, such as tin(II) chloride, as reducing agent.

The present invention also extends to the above reaction sequence, starting from compounds of formula IId, for the preparation of compounds of formula IIa and I by way of compounds of formula IIe.

Further details of such processes for the preparation of the starting compounds IIa and their precursors can be found in the Examples.

The compounds IIb wherein X is other than cyclopentyloxycarbonyloxy are known or can be prepared analogously to the known compounds.

The preparation of the starting material of formula IIc is carried out by reacting haloformic acid cyclopentyl ester, such as chloroformic acid cyclopentyl ester, in the presence of an amine, such as trialkylamine, e.g. N,N-dimethyl-N-octadecylamine, using an inorganic base, such as an alkali metal hydroxide, e.g. sodium hydroxide. The reaction is carried out preferably in an inert solvent, that is to say a solvent that does not take part in the reaction.

Variant b): $X_1$ is especially halogen, preferably iodine.

Corresponding compounds of formula III are reacted with a compound of formula H—C≡C—R (IIIa), the reaction advantageously being carried out with the addition of a copper(I) halide, especially copper(I) iodide, in the presence of a catalytic agent, such as a bis(triphenylphosphine)palladium(II)-dihalide, such as -dichloride. One of the bases mentioned hereinbefore or hereinafter, e.g. triethylamine, is also especially added.

A silyl radical Z is, for example, tri-lower alkylsilyl, such as trimethylsilyl.

If $X_1$ is a group of formula —C≡C—Z, corresponding compounds of formula III are treated, for example, with an inorganic base, such as an alkali metal, e.g. sodium hydroxide, and the reaction mixture is then hydrolysed by means of an acid, such as hydrochloric acid. Compounds of formula I are obtained in which R is hydrogen.

Compounds III and salts thereof can be obtained, for example, by converting a compound of formula IId (see above) in a manner known per se [see Variant c)] into a compound of formula IIIc

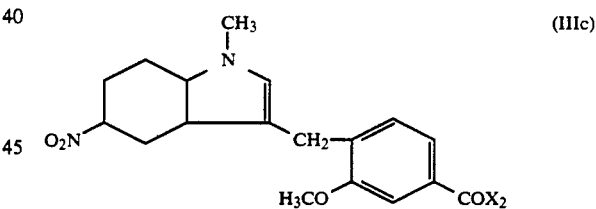
(IIIc)

wherein $X_2$ is the group (IVa'), the group (IVa'') or the group (IVa'''), and reacting that compound analogously to Variant c) with a compound of formula IIId

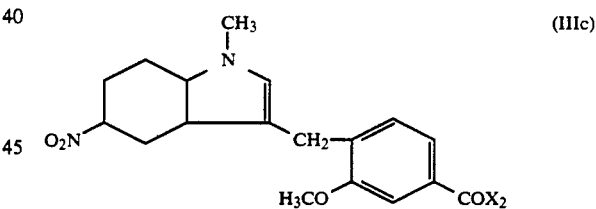
(IIId)

to form a compound of formula IIf

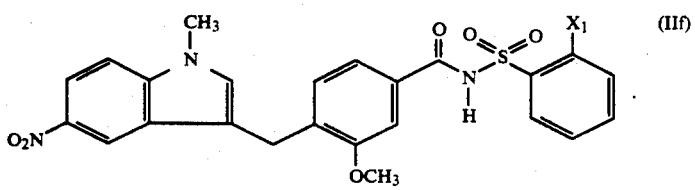

In the next reaction step the nitro group is reduced to an amino group in a manner familiar to the person skilled in the art, e.g. by catalytic hydrogenation in the presence of a hydrogenation catalyst, such as palladium-on-carbon or Raney nickel. This results in a compound of formula IIIe

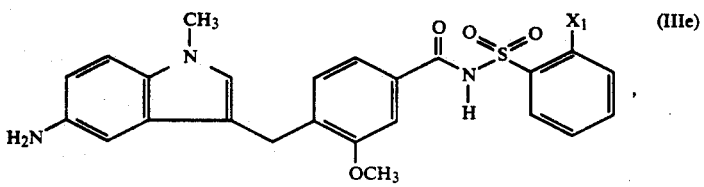

which is then reacted analogously to Variant a) with a compound of formula IIb (see above), especially a compound of formula IIc (see above).

In order to produce compounds of formula III it is alternatively possible, for example, first of all, in a compound of formula IIIc wherein $X_2$ is the group (IVa'), the group (IVa'') or the group (IVa'''), to reduce the nitro group to an amino group in a manner familiar to the person skilled in the art, e.g. by catalytic hydrogenation in the presence of a hydrogenation catalyst, such as palladium-on-carbon or Raney nickel, and then to react the carboxy derivative of formula IIIf

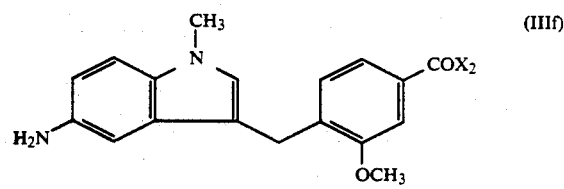

so obtainable with a compound of formula IIb (see above), especially a compound of formula IIc (see above), analogously to Variant a). The compound of formula IVa (see above) resulting therefrom is reacted analogously to Variant c) with a compound of formula IIId or with a salt thereof.

The activation of the carboxy group in compounds of formula IId-in order to prepare compounds of formula IIIc-is carried out preferably in the presence of a condensing agent, e.g. by reaction with a corresponding hydroxy compound, e.g.

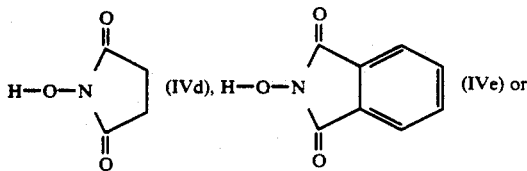

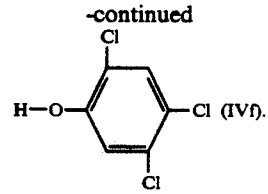

Suitable condensing agents are, for example, a carbodiimide, such as diethyl- or dicyclohexyl-carbodiimide, or, if the reaction is with 2,4,5-trichlorophenol, also a base, such as di-lower alkylaminopyridine, e.g. dimethylaminopyridine.

The reaction is carried out preferably in an ether, such as tetrahydrofuran or dioxane, a halogenated hydrocarbon, such as chloroform or carbon tetrachloride, or also an ester, such as ethyl acetate, or an amide, such as dimethylformamide.

In an advantageous variant, the reduction of a compound of formula IIIc and the reaction with a compound of formula IIc can be carried out in a one-pot process, that is to say without isolation of the intermediate of formula IIIf.

Further details of such processes for the preparation of the starting compounds III and their precursors are to be found in the Examples.

The present invention also extends to the above reaction sequences for the preparation of compounds of formula III and I starting from compounds of formula IId by way of compounds of formula IIIc, IIf and IIIe, or alternatively starting from a compound of formula IIIc by way of compounds of formula IIIf and/or IVa.

The starting material of formula IIIa is known or can be prepared in a manner known per se. Details can be found in the Examples.

Variant c):

The reaction according to Variant c) is carried out preferably in the presence of one of the bases mentioned hereinbefore, especially DBU.

The reaction is carried out preferably in an ether, such as tetrahydrofuran or dioxane, a halogenated hydrocarbon, such as chloroform or carbon tetrachloride, also an ester, such as ethyl acetate, or an amide, such as dimethylformamide.

The compounds IVa and salts thereof can be prepared, for example, as follows:

A compound of formula IIIc (see above) is used as starting material and the nitro group therein is reduced to an amino group in a manner familiar to the person skilled in the art, e.g. by catalytic hydrogenation in the presence of a hydrogenation catalyst, such as palladium-on-carbon or Raney nickel. In the next reaction step the compound of formula IIIf so obtainable (see above) is converted with a compound of formula IIb, especially a compound of formula IIc, into the relevant compound of formula IVa analogously to Variant a).

The reduction of the 5-nitroindole compound and the reaction with a compound of formula IIc can advantageously be carried out in a one-pot process, that is to say without isolation of a compound of formula IIIf.

The invention relates also to the novel compounds obtainable by the process variants above.

A compound of formula I or salt thereof obtainable in accordance with the invention or in another manner can be converted in a manner known per se into a different compound of formula I.

Compounds of formula I wherein $R_1$ is hydroxy can be acylated in a manner known per se to compounds of formula I wherein $R_1$ is $C_2-C_7$alkanoyloxy, for example analogously to the procedure described in Variant c), e.g. by reaction with the corresponding carboxylic acid or with a reactive derivative thereof. Such reactive derivatives are, for example, anhydrides, including mixed anhydrides, such as an acid halide, e.g. an acid chloride, or anhydrides with a formic acid ester, or activated carboxylic acid esters, such as cyano-methyl ester, (4)-nitrophenyl ester, polyhalophenyl ester, e.g. trichlorophenyl ester. The reaction with the carboxylic acid or a salt thereof is carried out under water-removing conditions, e.g. with azeotropic removal of the water of reaction, or by treatment with a suitable condensing agent, e.g. N,N'-dicyclohexylcarbodiimide. The reaction with a reactive acid derivative is advantageously carried out in the presence of a base.

By treatment with strong bases, such as alkali metal hydroxides, e.g. lithium hydroxide, $R_1=C_2-C_7$alkanoyloxy can be hydrolysed to $R_1=OH$.

If $R_1$ is hydroxy, this can be etherified in a manner known per se to compounds of formula I wherein $R_1$ is $C_1-C_7$alkoxy or phenyl-$C_1-C_7$alkoxy. The etherification can be carried out e.g. with an alcohol, such as an unsubstituted or substituted lower alkanol, or with a reactive ester thereof. Suitable reactive esters of the desired alcohols are, for example, those with strong inorganic or organic acids, such as corresponding halides, sulfates, lower alkanesulfonates or unsubstituted or substituted benzenesulfonates, e.g. chlorides, bromides, iodides or methane-, benzene- or p-toluene-sulfonates. The etherification can be carried out e.g. in the presence of a base, e.g. an alkali metal hydride, hydroxide or carbonate or a basic amine. Conversely, corresponding ethers, such as lower alkoxy compounds, can be cleaved e.g. by means of strong acids, such as mineral acids, e.g. hydrobromic or hydriodic acid, which may advantageously be in the form of pyridinium halides, or by means of Lewis acids, e.g. halides of elements of main group III or of corresponding sub-groups. The reactions can, if necessary, be carried out with cooling or heating, e.g. in a temperature range from approximately $-20°$ to approximately $+100°$ C., in the presence or absence of a solvent or diluent, under inert gas and/or under pressure and optionally in a closed vessel.

Corresponding ethers of formula I wherein $R_1$ is (phenyl-)$C_1-C_7$alkoxy can be cleaved in a manner known per se, e.g. by means of strong acids, such as mineral acids, e.g. hydrobromic or hydriodic acid, which may advantageously be in the form of pyridinium halides, or by means of Lewis acids, e.g. halides of elements of main group III or of corresponding sub-groups. The reactions can, if necessary, be carried out with cooling or heating, e.g. in a temperature range from approximately $-20°$ to approximately $+100°$ C., in the presence or absence of a solvent or diluent, under inert gas and/or under pressure and optionally in a closed vessel.

Salts of compounds I can be prepared in a manner known per se. For example acid addition salts of compounds I are obtained by treatment with a suitable acid or a suitable ion exchange reagent, and salts with bases by treatment with a suitable base or a suitable ion exchange reagent. Salts of compounds I can be converted in customary manner into the free compounds I; acid addition salts can be converted, for example, by treatment with a suitable basic agent or a suitable ion exchange reagent and salts with bases can be converted e.g. by treatment with a suitable acid or a suitable ion exchange reagent.

Salts of compounds I can be converted in a manner known per se into different salts of compounds I; acid addition salts, for example, can be converted into different acid addition salts e.g. by treating a salt of an inorganic acid, such as a hydrochloride, with a suitable metal salt, such as a sodium, barium or silver salt, of an acid, e.g. with silver acetate, in a suitable solvent in which a forming inorganic salt, e.g. silver chloride, is insoluble and thus separates out from the reaction mixture.

Depending on the procedure and reaction conditions, the compounds I with salt-forming properties may be obtained in free form or in the form of salts.

In view of the close relationship between the compound I in free form and in the form of its salts, hereinbefore and hereinafter any reference to the free compound I or its salts should be understood as including also the corresponding salts or the free compound I, respectively, where appropriate and expedient.

The compounds I, including the salts of salt-forming compounds, may also be obtained in the form of their hydrates and/or include other solvents, for example solvents that may have been used for the crystallisation of compounds that are in solid form.

Depending on the choice of starting materials and procedures, the compounds I and their salts may be in the form of one of the possible isomers or in the form of a mixture thereof. There are obtainable as pure isomers e.g. pure diastereoisomers. Similarly, the isomeric mixtures may be e.g. diastereoisomeric mixtures. Isomeric mixtures of compounds I in free form or in salt form obtainable in accordance with the process or by some other method can be separated into their components in customary manner, e.g. on the basis of the physico-chemical differences between their constituents in known manner by fractional crystallisation, distillation and/or chromatography. Advantageously the more active isomer is isolated.

The invention relates also to those embodiments of the process according to which a compound obtainable at any stage of the process as intermediate is used as starting material and the remaining steps are carried out, or a starting material is used in the form of a derivative or salt or, especially, is formed under the reaction conditions.

The starting materials and intermediates used in the process of the present invention are preferably those, each in free form or in salt form, that result in the compounds I and their salts described at the beginning as being especially valuable. The invention extends also to novel starting materials and intermediates, each in free or in salt form, for the preparation of compounds I and their salts, to their use and to processes for their preparation, the variable R being as defined for compounds I.

The invention relates also to the use of compounds I and their pharmaceutically acceptable salts for the treatment of allergic conditions and disorders, preferably in the form of pharmaceutically acceptable compositions, especially in a method for the therapeutic treatment of the animal or human body, and to such a treatment process.

The invention relates also to pharmaceutical compositions that comprise a compound I or a pharmaceutically acceptable salt thereof as active ingredient, and to processes for their preparation. The pharmaceutical compositions are those for enteral, such as oral, or also rectal, administration, those for parenteral administration, those for local administration and, especially, those for inhalation administration to warm-blooded animals, especially humans, comprising the pharmacological active ingredient on its own or together with customary pharmaceutical excipients.

The pharmaceutical compositions comprise (in % by weight) e.g. from approximately 0.001% to 100%, preferably from approximately 0.1% to approximately 50%, active ingredient.

Pharmaceutical compositions for enteral and parenteral administration are e.g. in unit dose forms, such as dragées, tablets, capsules or suppositories, and also ampoules. They are prepared in a manner known per se, e.g. by means of conventional mixing, granulating, confectioning, dissolving or lyophilising processes. For example, pharmaceutical compositions for oral administration can be obtained by combining the active ingredient with solid carriers, if desired granulating a resulting mixture, and processing the mixture or granules, if desired or necessary after the addition of appropriate excipients, to form tablets or dragée cores.

Suitable carriers are especially fillers, such as sugars, e.g. lactose, saccharose, mannitol or sorbitol, cellulose preparations and/or calcium phosphates, e.g. tricalcium phosphate or calcium hydrogen phosphate, and binders, such as starch pastes, using e.g. corn, wheat, rice or potato starch, gelatin, tragacanth, methylcellulose and/or polyvinylpyrrolidone, and, if desired, disintegrators, such as the above-mentioned starches, also carboxymethyl starch, crosslinked polyvinylpyrrolidone, agar, alginic acid or a salt thereof, such as sodium alginate. Excipients are especially flow conditioners and lubricants, e.g. silicic acid, talcum, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents or solvent mixtures, or, for the preparation of enteric coatings, solutions of suitable cellulose preparations, such as acetylcellulose phthalate or hydroxypropylmethylcellulose phthalate. Dyes or pigments may be added to the tablets or dragée coatings, e.g. for identification purposes or to indicate different doses of active ingredient.

Other orally administrable pharmaceutical compositions are dry-filled capsules consisting of gelatin, and also soft sealed capsules consisting of gelatin and a plasticiser, such as glycerol or sorbitol. The dry-filled capsules may contain the active ingredient in the form of granules, for example in admixture with fillers, such as lactose, binders, such as starches, and/or glidants, such as talcum or magnesium stearate, and, if desired, stabilisers. In soft capsules, the active ingredient is preferably dissolved or suspended in suitable liquids, such as fatty oils, paraffin oil or liquid polyethylene glycols, to which stabilisers may also be added.

Suitable rectally administrable pharmaceutical compositions are e.g. suppositories that consist of a combination of the active ingredient with a suppository base. Suitable suppository bases are e.g. natural or synthetic triglycerides, paraffin hydrocarbons, polyethylene glycols or higher alkanols. It is also possible to use gelatin rectal capsules, which contain a combination of the active ingredient with a base material. Suitable base materials are e.g. liquid triglycerides, polyethylene glycols or paraffin hydrocarbons.

For parenteral administration there are suitable, especially, aqueous solutions of an active ingredient in water-soluble form, e.g. in the form of a water-soluble salt, or also suspensions of the active ingredient, such as corresponding oily injection suspensions, there being used suitable lipophilic solvents or vehicles, such as fatty oils, e.g. sesame oil, or synthetic fatty acid esters, e.g. ethyl oleate or triglycerides, or aqueous injection suspensions that comprise viscosity-increasing substances, e.g. sodium carboxymethylcellulose, sorbitol and/or dextran, and, if desired, also stabilisers.

Pharmaceutical compositions for local administration are, e.g. for topical treatment of the skin, lotions, creams and ointments, that is to say liquid or semi-solid oil-in-water or water-in-oil emulsions, fatty ointments that are water-free, pastes, that is to say creams and ointments with secretion-absorbing powder constituents, gels, which are aqueous, have a low water content or are water-free and consist of swellable gel-forming materials, foams, that is to say liquid oil-in-water emulsions in aerosol form which are administered from pressurised containers, and tinctures having an aqueous-ethanolic base, each of which compositions may comprise further customary pharmaceutical excipients, such as preservatives. There are suitable for local treatment of the eyes, e.g. eyedrops that comprise the active ingredient in sterile aqueous or oily solution, and eye ointments, which preferably are also produced in sterile form. There are suitable for local treatment of the nose e.g. sprays, similar to the coarse powders described further below for the treatment of the respiratory tract, which are administered by rapid inhalation through the nostrils, and especially nose-drops, which comprise the active ingredient in aqueous or oily solution. There are suitable for local treatment of the buccal cavity e.g. lozenges and pastilles that comprise the active ingredient in an inert composition formed e.g. from sugar and gum arabic or tragacanth gum to which flavourings may be added. The preparation of the pharmaceutical compositions for local administration is carried out in a manner known per se by mixing the active ingredient with the pharmaceutical excipients, for example by dissolving or suspending the active ingredient in the base material or in a portion thereof, if necessary. In order to prepare emulsions in which the active ingredient is dissolved in one of the liquid phases, the active ingredient is usually dissolved therein before emulsification; in order to prepare suspensions in which the active ingredient is suspended in the emulsion, the active ingredient is mixed with a portion of the base material after emulsification and then added to the remainder of the formulation.

Pharmaceutical compositions for inhalation administration are those in which the active ingredient is in micronised form, that is to say in which the particle size of the active ingredient is less than 20 μm, especially less than 10 μm, and advantageously less than 5 μm, e.g. micronised powders and aerosols, which are administered in the form of sprays. The micronised powders comprise the active ingredient on its own or together with an inert carrier, such as lactose, advantageously together with one of the propellants mentioned below. Aerosols are solutions, suspensions or emulsions of the active ingredient in a suitable pharmaceutically acceptable liquid phase, such as in ethanol or water or an appropriate mixture, may as required also comprise other pharmaceutical excipients, such as non-ionic or anionic surface-active agents, emulsifiers and stabilisers, and/or active ingredients of a different nature, and comprise a propellant, e.g. an inert gas, such as butane, under elevated pressure, or especially a readily volatile liquid, preferably one that boils at below customary room temperature (e.g. between approximately −30° C. and approximately +10° C.) under normal pressure, such as an at least partially fluorinated polyhalogenated lower alkane, or a mixture of such liquids. In order to prepare pharmaceutical compositions in a form ready for administration by inhalation, an appropriate pharmaceutical composition is introduced together with the propellant into suitable containers, such as flasks or pressurised bottles, which are provided with a suitable spraying device, e.g. a valve. The valve is preferably a metering valve that on operation releases a predetermined amount of the container contents corresponding to a predetermined dose of active ingredient. For the preparation of the finished medicament form it is also possible for appropriate amounts of the pharmaceutical composition and of the propellant to be introduced into the containers separately and only then mixed together.

The dose of the active ingredient may depend upon various factors, such as the activity and duration of action of the active ingredient, the severity of the disorder to be treated and of its symptoms, the mode of administration, and the species, sex, age and weight and/or the individual condition of the warm-blooded animal. For a warm-blooded animal weighing approximately 75 kg, the proposed approximate daily dose is normally from approximately 10 mg to approximately 1500 mg, especially from approximately 25 mg to approximately 250 mg, where appropriate in several, where appropriate equal, partial doses.

The following Examples illustrate the invention described above without limiting the scope thereof in any way. Temperatures are in degrees Celsius. "DMSO" stands for "dimethyl sulfoxide".

EXAMPLE 1

N-[4-[5-(Cyclopentyloxycarbonylamino)-1-methyl-indol-3-yl-methyl]-3-methoxybenzoyl]-2-(5-methoxy-pent-1-yn-1-yl)-benzenesulfonamide 1.15 ml of 1,8-diazabicyclo[5.4.0]undec-7-ene (DBU) are added to a solution of 1.3 g of 4-[5-(cyclopentyloxycarbonylamino)-1-methyl-indol-3-yl-methyl]-3-methoxy-benzoic acid N-succinimide ester and 0.7 g of 2-(5-methoxy-pent-1-yn-1-yl)-benzenesulfonamide in 25 ml of methylene chloride. The mixture is stirred for 3 hours under argon and then diluted with 100 ml of methylene chloride. The methylene chloride phase is washed twice with 50 ml of 1N hydrochloric acid, with 50 ml of water and with 50 ml of saturated sodium chloride solution, dried over magnesium sulfate and concentrated by evaporation at 20 torr and 40°. The residue is chromatographed on 100 g of silica gel (Merck, Si 60, 40–63 μm), using ethyl acetate as eluant. The fractions comprising the title compound are concentrated by evaporation at 20 torr and 40°. In that manner a white amorphous solid is obtained. $^1$H-NMR (400 MHz, DMSO-d$_6$): 8.88 (s, b, 1H); 7.95 (m, 1H); 7.59 (d, 1H); 7.58 (d, 1H); 7.45 (d, b, 1H); 7.34 (m, b, 3H); 7.23 (d, 1H); 7.17 (d, d, 1H); 7.02 (d, 1H); 6.91 (s, 1H); 5.09 (m, 1H); 3.93 (s, 2H); 3.86 (s, 3H); 3.67 (s, 3H); 3.39 (t, 2H); 3.18 (s, 3H); 2.35 (t, 2H); 1.92–1.55 (m, 8H); 1.67 (m, 2H).

The starting material is prepared as follows:

a) 10.0 g of 3-methoxy-4-(1-methyl-5-nitro-indol-3-yl-methyl)-benzoic acid methyl ester (see EP 199543 or J. Med. Chem. 1990, 33, 1781) are dissolved in 240 ml of tetrahydrofuran and 180 ml of methanol. A solution of 4.2 g of lithium hydroxide-monohydrate in 70 ml of water is added to the solution. The mixture is stirred for 15 hours at room temperature and concentrated under 11 torr at 50° to a volume of approximately 50 ml. The concentrate is diluted with 50 ml of water and the solution is rendered acidic with 1N hydrochloric acid. The precipitated yellow crystals are filtered off, washed with 20 ml of water and dried for 20 hours under 0.01 torr at 40°. The 4-(1-methyl-5-nitro-indol-3-yl-methyl)-3-methoxy-benzoic acid melts at 263°–265°.

b) 1.23 g of N-hydroxysuccinimide and 2.38 g of dicyclohexylcarbodiimide are added to a suspension of 3.4 g of 4-(1-methyl-5-nitro-indol-3-yl-methyl)-3-methoxy-benzoic acid in 100 ml of tetrahydrofuran. That mixture is stirred for 16 hours at room temperature under argon. The reaction mixture is then filtered, the filtrate is concentrated by evaporation at 15 torr and 40°, the residue is dissolved in hot ethyl acetate and, on cooling, 3-methoxy-4-(1-methyl-5-nitro-indol-3-yl-methyl)-benzoic acid N-succinimide ester crystallises out in the form of yellow crystals, melting point 201°–203°.

3-Methoxy-4-(1-methyl-5-nitro-indol-3-yl-methyl)-benzoic acid N-succinimide ester can alternatively be prepared as follows:

36.0 g of 3-methoxy-4-methylbenzoic acid methyl ester are dissolved in 300 ml of methanol. 25 ml of 30% sodium hydroxide solution are added dropwise to the solution. The mixture is stirred for 16 hours at room temperature and for 3 hours at 40° and concentrated by evaporation under 11 torr at 50°. The residue is dissolved in 500 ml of water and the solution is rendered acidic (pH=1) with conc. hydrochloric acid. The precipitated white crystals are filtered off, washed with 40 ml of water and dried for 15 hours under 0.1 torr at 90°. The 3-methoxy-4-methylbenzoic acid melts at 157°–158°.

2.9 g of N-hydroxysuccinimide and 5.6 g of dicyclohexylcarbodiimide are added, with stirring, to a solution of 3.93 g of 3-methoxy-4-methylbenzoic acid in 100 ml of tetrahydrofuran under argon. The mixture is stirred at room temperature for 18 hours. The white suspension is filtered off and subsequently washed with 40 ml of tetrahydrofuran. The filtrate is concentrated to dryness by evaporation under 11 torr at 40°. The residue is dissolved in 30 ml of hot ethyl acetate. After cooling the solution and adding 10 ml of ether, 3-methoxy-4-methylbenzoic acid N-succinimide ester crystallises in the form of white crystals having a melting point of 134°–135°.

10.95 g of N-bromosuccinimide and 0.5 g of azoisobutyronitrile are added at room temperature, with stirring, to a suspension of 14.05 g of 3-methoxy-4-methylbenzoic acid N-succinimide ester in 160 ml of tetrahydrofuran under nitrogen. The mixture is heated under reflux for 24 hours, cooled to room temperature and filtered. The filtrate is concentrated by evaporation under 11 torr at 50°. The residue is crystallised from a mixture of 100 ml of ethyl acetate and 200 ml of hexane. The 4-bromomethyl-3-methoxy-benzoic acid N-succinimide ester melts at 124°–125°.

2.85 g of N-methyl-5-nitroindole and 7.5 g of silver carbonate are suspended, with stirring, in 100 ml of toluene in an argon atmosphere. The suspension is heated under reflux for 18 hours, cooled to 55°, and a solution of 5.4 g of 4-bromomethyl-3-methoxy-benzoic acid N-succinimide ester is added dropwise with stirring. The mixture is stirred for five days at 55°–60°, cooled to room temperature and filtered. The residue is then washed with 30 ml of toluene. The filtrate is concentrated by evaporation under 11 torr at 50°. The residue is chromatographed on 1000 g of silica gel over a MPLC-column (eluant: ethyl acetate/hexane 3:2). The 3-methoxy-4-(1-methyl-5-nitro-indol-3-yl-methyl)-benzoic acid N-succinimide ester obtainable in that manner is recrystallised from ethyl acetate. Yellow crystals having a melting point of 215°–216° are obtained.

c) 3.0 g of 3-methoxy-4-(1-methyl-5-nitro-indol-3-yl-methyl)-benzoic acid N-succinimide ester are dissolved in 60 ml of tetrahydrofuran and 0.6 g of 5% palladium on activated carbon are added. Hydrogenation is carried out for 10 hours at room temperature under normal pressure. The catalyst is then suction-filtered off using a glass frit, and subsequently washed with hot tetrahydrofuran. The filtrate is concentrated by evaporation at 15 torr and 40°. The resulting solid material is agitated with ethyl ether. After filtration, 3-methoxy-4-(1-methyl-5-amino-indol-3-yl-methyl)-benzoic acid N-succinimide ester is obtained in the form of beige crystals. $^1$H-NMR (200 MHz, DMSO-d$_6$): 7.61 (d, d, 1H); 7.55 (s, 1H); 7.23 (d, 1H); 7.09 (d, 1H); 6.92 (s, 1H); 6.50–6.60 (m, 2H); 4.50 (s, b, 2H); 3.96 (2S, 5H); 3.63 (s, 3H); 2.90 (s, 4H).

d) 1.8 g of N-methylmorpholine and 0.95 g of chloroformic acid cyclopentyl ester are added to a solution of 2.4 g of 3-methoxy-4-(1-methyl-5-amino-indol-3-yl-methyl)-benzoic acid N-succinimide ester in 70 ml of methylene chloride. The reaction mixture is stirred for 2 hours at room temperature under argon. 20 ml of ice-cold 1N hydrochloric acid are then added to the reaction mixture. The organic phase is removed and washed with 20 ml of 0.1N hydrochloric acid, with 30 ml of water and with 20 ml of saturated sodium chloride solution, dried (MgSO$_4$) and concentrated by evaporation at 15 torr and 40°. A light-red oil remains, which is crystallised from hot ethyl acetate. The 4-[5-(cyclopentyloxycarbonylamino)-1-methyl-indol-3-yl-methyl]-3-methoxy-benzoic acid N-succinimide ester melts at 195°–196°.

e) 2.4 g of sodium hydride dispersion in oil are suspended twice with 20 ml of hexane. The hexane is decanted off each time. 100 ml of tetrahydrofuran and then, within 5 minutes, 4.62 ml of pent-4-yn-1-ol dissolved in 30 ml of tetrahydrofuran, are added. The suspension is heated to 40° and stirred for 30 minutes, whereupon a solution of 3.42 ml of methyl iodide in 20 ml of tetrahydrofuran is added dropwise. The reaction mixture is stirred for 16 hours at room temperature under argon. The tetrahydrofuran is distilled off at normal pressure, and the residue is taken up in 100 ml of ether/water=1/1 and adjusted to pH 2 with 1N hydrochloric acid. In a separating funnel, the organic phase is removed and the aqueous phase is extracted twice with 20 ml of ether each time. The combined organic phases are washed with water and dried over magnesium sulfate and the solvent is evaporated off at normal pressure. Pent-4-yn-1-yl-methyl ether remains in the form of a yellow oil. The $^1$H-NMR shows a content of 60% pent-4-yn-1-yl-methyl ether in ethyl ether/tetrahydrofuran=1/1. $^1$H-NMR (200 MHz, DMSO-d$_6$): 3.37 (t, 2H); 3.23 (s, 3H); 2.77 (t, 1H); 2.19 (d, t, 2H); 1.68 (m, 2H).

The following may be prepared in an analogous manner:

But-3-yn-1-yl-methyl ether in the form of a 20% solution in tetrahydrofuran/ethyl ether=3/1. $^1$H-NMR (200 MHz, CDCl$_3$): 3.45 (m, 2H); 3.35 (s, 3H); 2.42 (m, 2H); 1.96 (t, 1H); starting from but-3-yn-1-ol.

Prop-2-yn-1-yl-methyl ether in the form of a 10% solution in tetrahydrofuran/ethyl ether=½. $^1$H-NMR (200 MHz, CDCl$_3$): 4.07 (m, 2H); 3.35 (s, 3H); 2.41 (t, 1H); starting from prop-2-yn-1-ol.

f) 135 ml of N,N-dimethylformamide and 22 ml of triethylamine are taken and 7.5 g of 2-iodobenzenesulfonamide, 2.6 g of pent-4-yn-1-yl-methyl ether as well as 0.067 g of copper(I) iodide and 0.144 g of bis(triphenylphosphine)palladium(II) dichloride are added. The reaction mixture is heated to 65° and stirred for 22 hours at that temperature under argon. After that time, the N,N-dimethylformamide is distilled off at 0.1 torr and 40°. The crude product is purified on 500 g of silica gel (Merck Si 60, 40–63 μm) with hexane/ethyl acetate=2/1 as eluant. The fractions containing the product are concentrated by evaporation at 15 torr and 40° to yield white crystalline 2-(5-methoxy-pent-1-yn-1-yl)-benzenesulfonamide, melting point: 59°–61°.

The following may be prepared in an analogous manner:

2-(Pent-1-yn-1-yl)-benzenesulfonamide, light-brown crystals. $^1$H-NMR (200 MHz, DMSO-d$_6$): 7.90 (d, d, 1H); 7.45–7.61 (m, 3H); 7.18 (s, 2H); 2.49 (t, 2H); 2.60 (m, 2H); 1.02 (t, 3H); starting from 2-iodobenzenesulfonamide and 1-pentyne.

2-(3-Methyl-but-1-yn-1-yl)-benzenesulfonamide, yellowish oil, which solidifies on standing. $^1$H-NMR (200 MHz, DMSO-d$_6$): 7.90 (d, d, 1H); 7.45–7.60 (m, 3H); 7.12 (s, 2H); 2.88 (m, 1H); 1.25 (s, 3H); 1.20 (s, 3H); starting from 2-iodobenzenesulfonamide and 3-methyl-1-butyne.

2-(3-Methoxy-prop-1-yn-1-yl)-benzenesulfonamide, yellowish oil, which solidifies on standing. $^1$H-NMR (200 MHz, CDCl$_3$): 8.02 (d, d, 1H); 7.59 (d, t, 1H); 7.40–7.55 (m, 2H); 5.30 (s, 2H); 4.38 (s, 2H); 3.48 (s, 3H); starting from 2-iodobenzenesulfonamide and 3-methoxy-prop-1-yne.

2-(4-Methoxy-but-1-yn-1-yl)-benzenesulfonamide, light-brown crystals. $^1$H-NMR (200 MHz, DMSO-d$_6$): 7.91 (d, d, 1H); 7.47–7.62 (m, 3H); 7.20 (s, 2H); 3.57 (t, 2H); 3.31 (s, 3H); 2.77 (t, 2H); starting from 2-iodobenzenesulfonamide and 4-methoxybutyne.

2-(5-Hydroxy-pent-1-yn-1-yl)-benzenesulfonamide, reddish oil. $^1$H-NMR (300 MHz, DMSO-d$_6$): 7.88 (d, d, 1H); 7.45–7.60 (m, 3H); 7.20 (s, 2H); 4.59 (t, 1H); 3.55 (q, 2H); 2.53 (t, 2H); 1.71 (m, 2H); starting from 2-iodobenzenesulfonamide and 5-hydroxypentyne.

2-(4-Hydroxy-but-1-yn-1-yl)-benzenesulfonamide, light-brown crystals. $^1$H-NMR (400 MHz, DMSO-d$_6$): 7.88 (d, d, 1H); 7.45–7.60 (m, 3H); 7.30 (s, b, 2H); 5.30 (s, b, 1H); 3.62 (6, 2H); 2.62 (t, 2H); starting from 2-iodobenzenesulfonamide and 4-hydroxybutyne.

2-(Hydroxy-prop-1-yn-1-yl)-benzenesulfonamide, white crystals. $^1$H-NMR (400 MHz, CDCl$_3$): 8.20 (d, d, 1H); 7.60 (d, d, 1H); 7.52 (d, t, 2H); 7.46 (d, t, 1H); 5.58 (s, 2H); 4.60 (s, 2H); starting from 2-iodobenzenesulfonamide and 3-hydroxypropyne.

2-(3-Hydroxy-but-1-yn-1-yl)-benzenesulfonamide, orange crystals. $^1$H-NMR (400 MHz, CDCl$_3$): 8.03 (d, d, 1H); 7.60 (d, d, 1H); 7.55 (d, t, 1H); 7.47 (d, t, 1H); 5.40 (s, 2H); 4.86 (q, 1H); 3.05 (s, b, 1H); 1.61 (d, 3H); starting from 2-iodobenzenesulfonamide and 3-hydroxybutyne.

2(4-Hydroxy-pent-1-yn-1-yl)-benzenesulfonamide, yellow oil. $^1$H-NMR (200 MHz, DMSO-d$_6$: 7.90 (d, d, 1H); 7.45–7.63 (m, 3H); 7.36 (s, 2H); 5.30 (d, 1H); 3.92 (m, 1H); 2.65 (d, d, 1H); 2.50 (d, d, 1H); 1.21 (d, 3H); starting from 2-iodobenzenesulfonamide and 4-hydroxypentyne.

EXAMPLE 2

N-[4-[5-(Cyclopentyloxycarbonylamino)-1-methyl-indol-3-yl-methyl]-3-methoxybenzoyl]-2-(5-methoxy-pent-1-yn-1-yl)-benzenesulfonamide can be prepared analogously to Example 1 starting from 4-[5-(cyclopentyloxycarbonylamino)-1-methyl-indol-3-yl-methyl]-3-methoxy-benzoic acid 2,4,5-trichlorophenyl ester (m.p. 134°–136°) and 2-(5-methoxy-pent-1-yn-1-yl)-benzenesulfonamide.

The starting material is prepared as follows:

1.66 g of dicyclohexylcarbodiimide are added with stirring, at room temperature, to a mixture of 2.38 g of 4-(1-methyl-5-nitro-indol-3-yl-methyl)-3-methoxy-benzoic acid, 1.48 g of 2,4,5-trichlorophenol and 1.0 g of 4-dimethylaminopyridine in 140 ml of tetrahydrofuran in a nitrogen atmosphere. The reaction mixture is stirred for 15 hours at room temperature and filtered. The filtrate is concentrated by evaporation under 11 torr at 50°. The residue is dissolved in 400 ml of chloroform with heating. The organic phase is washed at room temperature with 50 ml of 2N hydrochloric acid and 50 ml of water and dried over MgSO$_4$ and the solution is concentrated to dryness under 11 torr at 40°. The residue is chromatographed on 350 g of silica gel (eluant: dichloromethane). The 3-methoxy-4-(1-methyl-5-nitro-indol-3-yl-methyl)-benzoic acid 2,4,5-trichlorophenyl ester obtainable in that manner is suspended in 50 ml of ether and filtered off. Yellow crystals having a melting point of 235°–236° are obtained.

A suspension of 1.04 g of 3-methoxy-4-(1-methyl-5-nitro-indol-3-yl-methyl)-benzoic acid 2,4,5-trichlorophenylester, 0.6 g of dicyclopentyl dicarbonate and 1,2-dichlorobenzene in 60 ml of tetrahydrofuran is hydrogenated at room temperature for 25 hours after the addition of 04, g of palladium-oncarbon catalyst (10%). A further 0.8 g of catalyst and 0.5 g of 1,2-dichlorobenzene are added and hydrogenation is continued for a further 45 hours. In order to remove the catalyst the mixture is filtered and the residue is subsequently washed with 50 ml of tetrahydrofuran. The filtrate is concentrated to dryness by evaporation under 11 torr. The residue is triturated with 100 ml of petroleum ether, filtered off and chromatographed on 190 g of silica gel over a MPLC column (eluant: dichloromethane). The 4-[5-(cyclopentyloxycarbonylamino)-1-methyl-indol-3-yl-methyl]-benzoic acid 2,4,5-trichlorophenyl ester obtainable in that manner is recrystallised from ether/petroleum ether. Colourless crystals having a melting point of 134°–136° are obtained.

Preparation of dicyclopentyl dicarbonate: 15 mg of N,N-dimethyl-octadecylamine and then, with rapid stirring, a solution of 2.0 g of sodium hydroxide in 30 ml of water, are added at 20° to a solution of 8.29 g of chloroformic acid cyclopentyl ester in 64 ml of dichloromethane. The mixture is stirred for 20 minutes at 20°. The organic phase is removed, dried over calcium chloride and filtered, and the filtrate is stirred for 5 minutes with 1.0 g of Hyflo Super Cel, filtered, and the filtrate is concentrated to dryness under 11 torr at 30°. The readily volatile components are removed from the residue by distillation at 0.03 torr and 80°. The residue from distillation, dicyclopentyl dicarbonate, is in the form of a colourless liquid. Yield 80%, b.p. 106/0.03 torr (decomposition).

EXAMPLE 3

The following is prepared in a manner analogous to that described in Example 1:

N-[4-[5-(Cyclopentyloxycarbonylamino)-1-methyl-indol-3-yl-methyl]-3-methoxybenzoyl]-2-ethynyl-benzenesulfonamide, white amorphous solid: $^1$H-NMR (400 MHz, CDCl$_3$): 9.09 (s, b, 1H); 8.34 (m, 1H); 7.67 (m, 1H); 7.59 (m, 2H); 7.53 (b, 1H); 7.36 (d, 1H); 7.25–7.10 (m, 4H); 6.79 (s, 1H); 6.57 (b, 1H); 5.23 (m, 1H); 4.07 (s, 2H); 3.88 (s, 3H); 3.73 (s, 3H); 3.64 (3.64 (s, 1H); 1.97–1.58 (m, 8H); starting from 4-[5-(cyclopentyloxycarbonylamino)-1-methyl-indol-3-yl-methyl]-3-methoxy-benzoic acid N-succinimide ester and 2-ethynyl-benzenesulfonamide.

The starting material is prepared as follows:

a) After the addition of 23 g of Raney nickel, a solution of 226.7 g of 2-nitrobenzenesulfonamide [Beilstein, Volume 11 H, p.68; E I, p. 20; E III, p.115] in 2270 ml of methanol is hydrogenated for 5 hours at 30°–40° under normal pressure. In order to remove the catalyst, filtration is carried out through a glass fibre filter and the filtrate is concentrated by evaporation under 11 torr at 40°. The residue is stirred with 500 ml of ether/petroleum ether (1:1). The suspension is filtered and the crystals are washed with 100 ml of ether/petroleum ether. The 2-aminobenzenesulfonamide melts at 152°–155°.

b) 508 ml of conc. hydrochloric acid are added slowly to a suspension of 102.8 g of 2-aminobenzenesulfonamide in 508 ml of water, the batch is then cooled to −5° with rapid stirring and, over a period of 40 minutes, a solution of 39.5 g of sodium nitrite in 200 ml of water is added dropwise. The yellow solution is stirred for 1 hour at 0°, and 55 ml of methylene chloride and then a solution of 88.2 g of potassium iodide in 103 ml of water are added dropwise. The resulting suspension is stirred at room temperature for 15 hours. The orange-beige crystals are filtered off, washed with 40 ml of water and dissolved in 500 ml of hot methanol. With stirring, 1000 ml of water are added to the white solution and the batch is cooled to room temperature. The precipitated crystals are filtered off and dried under 0.1 torr at 25°. The 2-iodobenzenesulfonamide melts at 168°-169°.

c) 9.3 ml of triethylamine and 3.5 g of ethynyl-trimethylsilane are added, while stirring well, to a mixture of 8.80 g of 2-iodobenzenesulfonamide, 0.60 g of bis(triphenylphosphine)palladium(II) dichloride and 0.30 g of copper(I) iodide in 15 ml of dimethylformamide. The mixture is stirred for 3 hours at 30° and poured onto 100 ml of ice/water. The suspension is extracted 3 times with 100 ml of ethyl acetate each time. The combined organic phases are washed with 50 ml of water and 50 ml of brine, dried over magnesium sulfate and concentrated by evaporation under 11 torr at 40°. The residue is chromatographed on 300 g of silica gel. Fractions 1-3, eluted with ethyl acetate/hexane (1:1), are discarded. Fractions 4-7, eluted with the same mixtures, are combined and concentrated by evaporation under 0.1 torr at 40°, 2-(2-trimethylsilyl-ethynyl)-benzenesulfonamide crystallising. The crystals are filtered off. M.p. 76°.

d) With gentle cooling and stirring, a solution of 3.4 g of 2-(2-trimethylsilyl-ethynyl)-benzene sulfonamide is 10 ml of methanol is added dropwise to 20 ml of 1N sodium hydroxide solution. The mixture is stirred for one hour at room temperature and acidified with 15 ml of 2N hydrochloric acid. The suspension is extracted three times with 70 ml of ethyl acetate each time. The combined organic phases are washed with 40 ml of water, dried over magnesium sulfate and concentrated under 11 torr at 40°. The precipitated colourless crystals are filtered off and dried for 15 hours under 0.1 torr at 40°. The 2-ethynyl-benzenesulfonamide melts at 130°.

The 2-ethynyl-benzenesulfonamide starting material can alternatively be prepared as follows:

a) 100 mg of copper(I) iodide and 220 mg of bis(triphenylphosphine)palladium(II) dichloride are added at room temperature, with stirring, to a mixture of 11.8 g of 2-iodobenzenesulfonamide, 4.2 ml of 2-methyl-3-butyn-2-ol and 50 ml of triethylamine in 200 ml of dimethylformamide. The mixture is stirred for 13 hours at 70° and concentrated by evaporation under 0.1 torr at 50°. The dark residue is dissolved hot in 100 ml of ethyl acetate/ethanol (1:1). The hot solution is stirred with activated carbon, filtered and cooled. After the addition of ether, colourless crystals precipitate. The crystals are filtered off and dried for 15 hours under 0.1 torr at 50°. The 2-(3-hydroxy-3-methyl-but-1-yn-1-yl)-benzenesulfonamide melts at 201°-202°.

b) 1.5 g of pulverised potassium hydroxide are added at room temperature, with stirring, to a solution of 3.0 g of 2-(3-hydroxy-3-methyl-but-1-yn-1-yl)-benzenesulfonamide in 40 ml of toluene. The mixture is then stirred for 3 hours at 70°, cooled, and poured onto a mixture of 50 ml of ice-water and 6 ml of 2N hydrochloric acid. The organic phase is removed, washed with 20 ml of water, dried over magnesium sulfate, and concentrated by evaporation under 11 torr at 50°. The residue is crystallised from ethyl acetate. The 2-ethynyl-benzenesulfonamide melts at 130°.

EXAMPLE 4

The following is prepared in a manner analogous to that described in Example 1:

N-[4-[5-(cyclopentyloxycarbonylamino)-1-methyl-indol-3-yl-methyl]-3-methoxybenzoyl]-2-(prop-1-yn-1-yl)-benzenesulfonamide, white amorphous solid: $^1$H-NMR (400 MHz, DMSO-$d_6$): 8.89 (s, b, 1H); 8.05 (m, 1H); 7.57 (m, 2H); 7.53 (m, 3H); 7.43 (d, d, 1H); 7.24 (d, 1H); 7.16 (d, d, 1H); 7.14 (d, 1H); 6.97 (s, 1H); 5.08 (m, 1H); 3.96 (s, 2H); 3.92 (s, 3H); 3.68 (s, 3H); 2.04 (s, 3H); 1.90-1.55 (m, 8H); starting from 4-[5-(cyclopentyloxycarbonylamino)-1-methyl-indol-3-yl-methyl]-3-methoxy-benzoic acid N-succinimide ester and 2-(prop-1-yn-1-yl)-benzenesulfonamide.

EXAMPLE 5

The following is prepared in a manner analogous to that described in Example 1:

N-[4-[5-(Cyclopentyloxycarbonylamino)-1-methyl-indol-3-yl-methyl]-3-methoxybenzoyl]-2-(but-1-yn-1-yl)-benzenesulfonamide, white amorphous solid: $^1$H-NMR (400 MHz, DMSO-$d_6$): 8.85 (s, b, 1H); 8.0 (d, 1H); 7.58 (m, 2H); 7.45 (n, 4H); 7.23 (d, 1H); 7.16 (d, d, 1H); 7.05 (d, 1H); 6.91 (s, 1H); 5.08 (m, 1H); 3.94 (s, 2H); 3.88 (s, 3H); 3.67 (s, 3H); 2.34 (q, 2H); 1.06 (t, 3H); 1.90-1.54 (m, 8H); starting from 4-[5-(cyclopentyloxycarbonylamino)-1-methyl-indol-3-yl-methyl]-3-methoxy-benzoic acid N-succinimide ester and 2-(but-1-yn-1-yl)-benzenesulfonamide.

The starting material is prepared as follows:

0.1 g of bis(triphenylphosphine)palladium(II) chloride, 0.05 g of copper iodide and 18.5 ml of triethylamine are added to a solution of 5 g of 2-iodobenzenesulfonamide in 70 ml of N,N-dimethylformamide. At room temperature, argon and 1-butyne are slowly introduced. After 18 hours the thin-layer chromatogram no longer shows any 2-iodobenzenesulfonamide. The dimethylformamide is evaporated off at 0.1 torr and 40°, and the residue is chromatographed on 300 g of silica gel (Merck ST 60, 40-63 μm). Methylene chloride is used as eluant. In that manner, after concentration of the product-containing fractions at 15 torr and 40°, white pulverulent 2-(but-1-yn-1-yl)-benzenesulfonamide is obtained: $^1$H-NMR (300 MHz, CDCl$_3$): 8.0 (d, d, 1H); 7.35 (d, d, 1H); 7.29 (d, t, 1H); 7.23 (d, t, 1H); 5.13 (s, 2H); 2.32 (q, 2H); 1.18 (t, 3H).

The following may be prepared in an analogous manner:

2-(Prop-1-yn-1-yl)-benzenesulfonamide, white crystals having a melting point of 158°-160°, starting from 2-iodobenzenesulfonamide and propyne gas.

EXAMPLE 6

The following is prepared in a manner analogous to that described in Example 1:

N-[4-[5-(cyclopentyloxycarbonylamino)-1-methyl-indol-3-yl-methyl]-3-methoxybenzoyl]-2-(pent-1-yn-1-yl)-benzenesulfonamide, white amorphous solid: $^1$H-NMR (400 MHz, DMSO-$d_6$): 8.76 (s, b, 1H); 8.00 (d, 1H); 7.56 (m, 2H); 7.44 (m, 4H); 7.21 (d, 1H); 7.16 (d, d, 1H); 7.08 (d, 1H); 6.91 (s, 1H); 5.07 (m, 1H); 3.94 (s, 2H); 3.88 (s, 3H); 3.66 (s, 3H); 2.33 (t, 2H); 1.90-1.53 (m, 8H); 1.47 (m, 2H); 0.89 (t, 3H); starting from 4-[5-(cyclopentyloxycarbonylamino)-1-methyl-indol-3-yl-methyl]-3-methoxy-benzoic acid N-succinimide ester and 2-(pent-1-yn-1-yl)-benzenesulfonamide.

EXAMPLE 7

The following is prepared in a manner analogous to that described in Example 1:

N-[4-[5-(cyclopentyloxycarbonylamino)-1-methyl-indol-3-yl-methyl]-3-methoxybenzoyl]-2-(3-methyl-but-1-yn-1-yl)-benzenesulfonamide, white amorphous solid: $^1$H-NMR (400 MHz, DMSO-$d_6$): 8.78 (b, 1H); 8.03 (n, 1H); 7.58 (m, 2H); 7.54-7.44 (n, 4H); 7.23 (d, 1H); 7.18 (d, d, 1H); 7.13 (d, 1H); 6.93 (s, 1H); 5.09 (m, 1H); 3.97

(s, 2H); 3.90 (s, 3H); 3.68 (s, 3H); 2.77 (m, 1H); 1.91–1.56 (m, 8H); 1.14 (d, 6H); starting from 4-[5-(cyclopentyloxycarbonylamino)-1-methyl-indol-3-yl-methyl]-3-methoxy-benzoic acid N-succinimide ester and 2-(3-methyl-but-1-yn-1-yl)-benzenesulfonamide.

EXAMPLE 8

The following is prepared in a manner analogous to that described in Example 1:

N-[4-[5-(cyclopentyloxycarbonylamino)-1-methyl-indol-3-yl-methyl]-3-methoxybenzoyl]-2-(5-acetoxy-pent-1-yn-1-yl)-benzenesulfonamide, white amorphous solid: $^1$H-NMR (400 MHz, DMSO-$d_6$): 8.76 (s, b, 1H); 8.02 (d, b, 1H); 7.58 (d, 1H); 7.56 (d, 1H); 7.53–7.45 (m, b, 3H); 7.44 (d, d, 1H); 7.23 (d, 1H); 7.17 (d, d, 1H); 7.12 (d, 1H); 6.93 (s, 1H); 5.09 (m, 1H); 4.07 (t, 2H); 3.96 (s, 2H); 3.90 (s, 3H); 3.68 (s, 3H); 2.46 (t, 2H); 1.95 (s, 3H); 1.91–1.55 (m, 8H); 1.78 (m, 2H); starting from 4-[5-(cyclopentyloxycarbonylamino)-1-methyl-indol-3-yl-methyl]-3-methoxy-benzoic acid N-succinimide ester and 2-(5-acetoxy-pent-1-yn-1-yl)-benzenesulfonamide.

The starting material and analogous starting material may be prepared as follows: 3.0 g of 2-(5-hydroxypent-1-yn-1-yl)-benzenesulfonamide and 4.7 ml of pyridine are dissolved at 45° in 200 ml of benzene. The solution is cooled to room temperature and 1.23 ml of acetyl chloride and 3.2 ml of triethylamine are added. The batch is stirred for 1 hour at room temperature under argon until the thin layer chromatogram no longer shows any starting material. The solvent is evaporated off at 15 torr and 40°. A mixture of ethyl acetate, water and 1N hydrochloric acid (100 ml) is added to the residue. In a separating funnel, after shaking, the organic phase is removed and washed with 0.1N hydrochloric acid and with saturated sodium chloride solution, dried (over magnesium sulfate) and concentrated by evaporation at 15 torr and 40°. The crude product is purified on 200 g of silica gel (Merck, ST 60, 40–63 μm) with hexane/ethyl acetate = 1/1 as eluant to yield 2-(5-acetoxy-pent-1-yn-1-yl)-benzenesulfonamide in the form of white crystals. The melting point is 66°–68°. $^1$H-NMR (300 MHz, DMSO-$d_6$): 7.87 (d, d, 1H); 7.45–7.60 (m, 3H); 7.20 (s, 2H); 4.13 (t, 2H); 2.57 (t, 2H); 2.02 (S, 3H); 1.86 (m, 2H).

The following may be prepared in an analogous manner:

2-(3-Acetoxy-prop-1-yn-1-yl)-benzenesulfonamide, white crystals, melting point 136°–138°, starting from 2-(3-hydroxy-prop-1-yn-1-yl)-benzenesulfonamide.

2-(4-Acetoxy-but-1-yn-1-yl)-benzenesulfonamide, colourless oil. $^1$H-NMR (200 MHz, CDCl$_3$): 4.35 (t, 2H); 2.87 (t, 2H); 2.15 (s, 3H); starting from 2-(4-hydroxy-but-1-yn-1-yl)-benzenesulfonamide.

EXAMPLE 9

The following is prepared in a manner analogous to that described in Example 1:

N-[4-[5-(cyclopentyloxycarbonylamino)-1-methyl-indol-3-yl-methyl]-3-methoxybenzoyl]-2-(4-acetoxy-but-1-yn-1-yl)-benzenesulfonamide, white amorphous solid: $^1$H-NMR (400 MHz, DMSO-$d_6$): 8.88 (s, b, 1H); 8.0 (m, 1H); 7.59 (d, 1H); 7.57 (d, 1H); 7.44 (m, 4H); 7.23 (d, 1H); 7.17 (d, d, 1H); 7.07 (d, 1H); 6.92 (s, 1H); 5.08 (m, 1H); 4.11 (t, 2H); 3.94 (s, 2H); 3.88 (s, 3H); 3.68 (s, 3H); 2.69 (t, 2H); 1.96 (s, 3H); 1.91–1.56 (m, 8H); starting from 4-[5-(cyclopentyloxycarbonylamino)-1-methyl-indol-3-yl-methyl]-3-methoxy-benzoic acid N-succinimide ester and 2-(4-acetoxy-but-1-yn-1-yl)-benzenesulfonamide.

EXAMPLE 10

The following is prepared in a manner analogous to that described in Example 1:

N-[4-[5-(cyclopentyloxycarbonylamino)-1-methyl-indol-3-yl-methyl]-3-methoxybenzoyl]-2-(3-acetoxy-prop-1-yn-1-yl)-benzenesulfonamide, white amorphous solid: $^1$H-NMR (400 MHz, DMSO-$d_6$): 8.89 (s, b, 1H); 8.09 (m, 1H); 7.62 (m, 3H); 7.58 (d, 1H); 7.54 (d, 1H); 7.43 (d, d, 1H); 7.24 (d, 1H); 7.16 (d, d, 1H); 7.13 (d, 1H); 6.97 (s, 1H); 5.08 (m, 1H); 4.92 (s, 2H); 3.97 (s, 2H); 3.92 (s, 3H); 3.69 (s, 3H); 1.95 (s, 3H); 1.91–1.55 (m, 8H); starting from 4-[5-(cyclopentyloxycarbonylamino)-1-methyl-indol-3-yl-methyl]-3-methoxy-benzoic acid N-succinimide ester and 2-(3-acetoxy-prop-1-yn-1-yl)-benzenesulfonamide.

EXAMPLE 11

The following is prepared in a manner analogous to that described in Example 1:

N-[4-[5-(cyclopentyloxycarbonylamino)-1-methyl-indol-3-yl-methyl]-3-methoxybenzoyl]-2-(4-acetoxy-pent-1-yn-1-yl)-benzenesulfonamide, white amorphous solid: $^1$H-NMR (400 MHz, DMSO-$d_6$); 8.76 (b, 1H); 7.98 (m, 1H); 7.59 (b, 2H); 7.46 (d, d, 1H); 7.37 (m, 3H); 7.22 (d, 1H); 7.18 (d, d, 1H); 7.04 (d, 1H); 6.89 (s, 1H); 5.09 (m, 1H); 4.91 (m, 1H); 3.94 (s, 2H); 3.86 (s, 3H); 3.67 (s, 3H); 2.61 (m, 2H); 1.95 (s, 3H); 1.92–1.55 (m, 8H); 1.31 (d, 3H); starting from 4-[5-(cyclopentyloxycarbonylamino)-1-methyl-indol-3-yl-methyl]-3-methoxy-benzoic acid N-succinimide ester and 2-(4-acetoxy-pent-1-yn-1-yl)-benzenesulfonamide.

The starting material and analogous starting material may be prepared as follows:

1 g of 2-(4-hydroxy-pent-1-yn-1-yl)-benzenesulfonamide is dissolved in 9 ml of pyridine and cooled to 5°, and 0.44 ml of acetic anhydride is added. The reaction mixture is stirred under argon at 5° for 14 hours and then at room temperature for a further 24 hours. The reaction mixture is then poured onto 100 ml of ice-cold 1N hydrochloric acid and extracted twice with 50 ml of ethyl acetate each time. The combined organic phases are washed twice with 20 ml of 1N hydrochloric acid each time, with 50 ml of water and with 30 ml of saturated sodium chloride solution, dried over magnesium sulfate, filtered off and concentrated by evaporation at 15 torr and 40°. The crude product is chromatographed on 80 g of silica gel (Merck ST 60, 40–63 μm). A 1/1 mixture of hexane and ethyl acetate is used as eluant. 2-(4-Acetoxy-pent-1-yn-1-yl)-benzenesulfonamide is obtained in the form of a colourless oil. $^1$H-NMR (200 MHz, DMSO-$d_6$): 7.90 (d, d, 1H); 7.48–7.63 (m, 3H); 7.22 (s, 2H); 5.01 (m, 1H); 2.82 (d, 2H); 2.05 (s, 3H); 1.33 (d, 3H).

The following may be prepared in an analogous manner:

2-(3-acetoxy-but-1-yn-1-yl)-benzenesulfonamide, colourless oil. $^1$H-NMR (200 MHz, CDCl$_3$): 8.03 (d, d, 1H); 7.40–6.70 (m, 3H); 5.50 (s, 2H); 5.45 (q, 1H); 2.13 (s, 3H); 1.65 (d, 3H); starting from 2-(3-hydroxy-but-1-yn-1-yl)-benzenesulfonamide.

EXAMPLE 12

The following is prepared in a manner analogous to that described in Example 1:

N-[4-[5-(cyclopentyloxycarbonylamino)-1-methyl-indol-3-yl-methyl]-3-methoxybenzoyl]-2-(5-pivaloyloxy-pent-1-yn-1-yl)-benzenesulfonamide, white amorphous solid: $^1$H-NMR (400 MHz, DMSO-d$_6$): 8.00 (m, 1H); 7.58 (d, 1H); 7.57 (d, 1H); 7.46 (d, d, 1H); 7.41 (m, 3H); 5.09 (m, 1H); 4.11 (t, 2H); 3.95 (s, 2H); 3.87 (s, 3H); 3.68 (s, 3H); 2.43; starting from 4-[5-(cyclopentyloxycarbonylamino)-1-methyl-indol-3-yl-methyl]-3-methoxy-benzoic acid N-succinimide ester and 2-(5-pivaloyloxy-pent-1-yn-1-yl)-benzenesulfonamide.

The starting material is prepared as follows:

2.0 g of 2-(5-hydroxy-pent-1-yn-1-yl)-benzenesulfochloride and 3.13 ml of pyridine are dissolved at 45° in 200 ml of benzene. The solution is cooled to room temperature and 1.41 ml of pivalic acid chloride as well as 2.15 ml of triethylamine are added. The batch is stirred at room temperature under argon for 0.5 hour until the thin-layer chromatogram no longer shows any starting material. The solvent is evaporated off at 15 torr and 40°. A mixture of ethyl acetate, water and 1N hydrochloric acid is added to the residue. In a separating funnel, after shaking, the organic phase is removed and washed with 0.1N hydrochloric acid and with saturated sodium chloride solution, dried over magnesium sulfate and concentrated by evaporation at 15 torr and 40°. The crude product is purified on 200 g of silica gel (Merck, ST 60, 40-63 μm) with hexane/ethyl acetate=1/1 as eluant to yield 1.0 g of 2-(5-pivaloyloxy-pent-1-yn-1-yl)-benzenesulfonamide in the form of a yellowish oil. $^1$H-NMR (400 MHz, DMSO-d$_6$): 7.88 (d, d, 1H); 7.47-7.60 (m, 3H); 7.18 (s, 2H); 4.16 (t, 2H); 2.57 (6, 2H); 1.90 (m, 2H); 1.08 (s, 9H).

The following may be prepared in an analogous manner:

2-(4-Pivaloyloxy-but-1-yn-1-yl)-benzenesulfonamide, white crystals having a melting point of 79°-80° C. $^1$H-NMR (200 MHz, DMSO-d$_6$): 7.90 (d, d, 1H); 7.48-7.62 (m, 3H); 7.22 (s, 2H); 4.22 (t, 2H); 2.86 (t, 2H); 1.08 (s, 9H).

2-(3-Pivaloyloxy-but-1-yn-1-yl)-benzenesulfonamide, yellow crystals. $^1$H-NMR (200 MHz, DMSO-d$_6$): 7.88 (d, d, 1H); 7.51-7.70 (m, 3H); 7.23 (s, 2H); 5.00 (s, 2H) 1.20 (s, 9H).

EXAMPLE 13

The following is prepared in a manner analogous to that described in Example 1:

N-[4-[5-(cyclopentyloxycarbonylamino)-1-methyl-indol-3-yl-methyl]-3-methoxybenzoyl]-2-(4-pivaloyloxy-but-1-yn-1-yl)-benzenesulfonamide, white amorphous solid: $^1$H-NMR (400 MHz, DMSO-d$_6$): 9.0 (b, 1H); 8.02 (d, b, 1H); 7.59 (d, 1H); 7.56 (d, 1H); 7.48 (m, b, 3H); 7.43 (d, d, 1H); 7.24 (d, 1H); 7.16 (d, d, 1H); 7.08 (d, b, 1H); 6.95 (s, 1H); 5.07 (m, 1H); 4.11 (t, 2H); 3.93 (s, 2H); 3.89 (s, 3H); 3.68 (s, 3H); 2.72 (t, b, 2H); 1.90-1.54 (m, 8H); 1.10 (s, 9H); starting from 4-[5-(cyclopentyloxycarbonylamino)-1-methyl-indol-3-yl-methyl]-3-methoxy-benzoic acid N-succinimide ester and 2-(4-pivaloyloxy-but-1-yn-1-yl)-benzenesulfonamide.

EXAMPLE 14

The following is prepared in a manner analogous to that described in Example 1:

N-[4-[5-(cyclopentyloxycarbonylamino)-1-methyl-indol-3-yl-methyl]-3-methoxybenzoyl]-2-(3-pivaloyloxy-prop-1-yn-1-yl)-benzenesulfonamide, white amorphous solid: $^1$H-NMR (400 MHz, DMSO-d$_6$): 8.89 (b, 1H); 8.08 (m, 1H); 7.60 (m, b, 3H); 7.58 (d, 1H); 7.54 (d, 1H); 7.43 (d, d, 1H); 7.24 (d, 1H); 7.17 (d, d, 1H); 7.12 (d, 1H); 6.97 (s, 1H); 5.08 (m, 1H); 4.93 (s, 2H); 3.96 (s, 2H); 3.91 (s, 3H); 3.68 (s, 3H); 1.90-1.55 (m, 8H); 1.11 (s, 9H); starting from 4-[5-(cyclopentyloxycarbonylamino)-1-methyl-indol-3-yl-methyl]-3-methoxy-benzoic acid N-succinimide ester and 2-(3-pivaloyloxy-prop-1-yn-1-yl)-benzenesulfonamide.

EXAMPLE 15

The following is prepared in a manner analogous to that described in Example 1:

N-[4-[5-(cyclopentyloxycarbonylamino)-1-methyl-indol-3-yl-methyl]-3-methoxybenzoyl]-2-(3-hydroxy-3-methyl-but-1-yn-1-yl)-benzenesulfonamide, white amorphous solid: $^1$H-NMR (400 MHz, DMSO-d$_6$); 8.74 (s, b, 1H); 8.03 (d, d, 1H); 7.57 (d, d, 1H); 7.55 (d, 1H); 7.53 (d, 1H); 7.54-7.44 (m, 2H); 7.42 (d, d, 1H); 7.21 (d, 1H); 7.16 (d, d, 1H); 7.10 (d, 1H); 6.91 (s, 1H); 5.08 (m, 1H); 3.95 (s, 2H); 3.88 (s, 3H); 3.66 (s, 3H); 1.91-1.52 (m, 8H); 1.41 (s, 6H); starting from 4-[5-(cyclopentyloxycarbonylamino)-1-methyl-indol-3-yl-methyl]-3-methoxy-benzoic acid N-succinimide ester and 2-(3-hydroxy-3-methyl-but-1-yn-1-yl)-benzenesulfonamide.

EXAMPLE 16

The following is prepared in a manner analogous to that described in Example 1:

N-[4-[5-(cyclopentyloxycarbonylamino)-1-methyl-indol-3-yl-methyl]-3-methoxybenzoyl]-2-(3-methoxy-prop-1-yn-1-yl)-benzenesulfonamide, white amorphous solid: $^1$H-NMR (400 MHz, DMSO-d$_6$): 8.88 (s, b, 1H); 7.98 (m, 1H); 7.58 (d, 1H); 7.57 (d, 1H); 7.44 (d, d, 1H); 7.40 (m, 3H); 7.23 (d, 1H); 7.17 (d, d, 1H); 7.02 (d, 1H); 6.91 (s, 1H); 5.09 (m, 1H); 4.21 (s, 2H); 3.93 (s, 2H); 3.86 (s, 3H); 3.68 (s, 3H); 3.29 (s, 3H); 1.91-1.55 (m, 8H); starting from 4-[5-(cyclopentyloxycarbonylamino)-1-methyl-indol-3-yl-methyl]-3-methoxy-benzoic acid N-succinimide ester and 2-(3-methoxy-prop-1-yn-1-yl)-benzenesulfonamide.

EXAMPLE 17

The following is prepared in a manner analogous to that described in Example 1:

N-[4-[5-(cyclopentyloxycarbonylamino)-1-methyl-indol-3-yl-methyl]-3-methoxybenzoyl]-2-(4-methoxy-but-1-yn-1-yl)-benzenesulfonamide, white amorphous solid: $^1$H-NMR (400 MHz, DMSO-d$_6$): 8.76 (b, 1H); 8.06 (m, 1H); 7.58 (d, 1H); 7.54 (d, 1H); 7.60-7.50 (m, 3H); 7.43 (d, d, 1H); 7.23 (d, 1H); 7.17 (d, d, 1H); 7.15 (d, 1H); 6.95 (s, 1H); 5.09 (m, 1H); 3.98 (s, 2H); 3.92 (s, 3H); 3.68 (s, 3H); 3.44 (t, 2H); 3.20 (s, 3H); 2.64 (t, 2H); 1.92-1.55 (m, 8H); starting from 4-[5-(cyclopentyloxycarbonylamino)-1-methyl-indol-3-yl-methyl]-3-methoxy-benzoic acid N-succinimide ester and 2-(4-methoxy-but-1-yn-1-yl)-benzenesulfonamide.

EXAMPLE 18

A solution of 0.39 g of chloroformic acid cyclopentyl ester in 20 ml of dichloromethane is added to a solution of 1.43 g of N-[4-(5-amino-1-methyl-indol-3-yl-methyl)-3-methoxybenzoyl]-2-(5-methoxy-pent-1-yn-1-yl)-benzenesulfonamide in 10 ml of dichloromethane and 0.78 g of N-methylmorpholine. The mixture is stirred for 3 hours at room temperature with the introduction of nitrogen, and is washed with 10 ml 1N hydrochloric acid and 10 ml of water. The organic phase is removed, dried over magnesium sulfate and concentrated by evaporation under 11 torr at 40°. The residue, a yellow foam, is subjected to flash chromatography on 100 g of silica gel. Fractions 1-5, each eluted with 50 ml of hexane/ethyl acetate (1:2), are discarded. Fractions 6-9, each eluted with 50 ml of ethyl acetate, are combined and concentrated by evaporation under 11 torr at 40°. The N-[4-[5-(cyclopentyloxycarbonylamino)-1-methyl-indol-3-yl-methyl]-3-methoxybenzoyl]-2-(5-methoxy-pent-1-yn-1-yl)benzenesulfonamide is in the form of a yellowish powder. $^1$H-NMR (400 MHz, DMSO-d$_6$): 8.88 (s, b, 1H); 7.95 (m, 1H); 7.59 (d, 1H); 7.58 (d, 1H); 7.45 (d, b, 1H); 7.34 (m, b, 3H); 7.23 (d, 1H); 7.17 (d, d, 1H); 7.02 (d, 1H); 6.91 (s, 1H); 5.09 (m, 1H); 3.93 (s, 2H); 3.86 (s, 3H); 3.67 (s, 3H); 3.39 (t, 2H); 3.18 (s, 3H); 2.35 (t, 2H); 1.92-1.55 (m, 8H); 1.67 (m, 2H).

The starting material is prepared as follows:

a) A solution of 5.0 g of 3-methoxy-4-(1-methyl-5-nitro-indol-3-yl-methyl)-benzoic acid in 250 ml tetrahydrofuran is added at room temperature, with stirring and with the introduction of argon to a mixture of 3.4 g of N-(3-dimethylaminopropyl)-N'-ethylcarbodiimide hydrochloride, 3.95 g of 2-iodobenzenesulfonamide and 2.15 g of 4-dimethylaminopyridine in 150 ml of dichloromethane. The mixture is stirred for 5 hours at 42° and then for 15 hours at room temperature. The precipitated yellow crystals are filtered off and dissolved in 200 ml of trichloromethane/methanol (9:1), with heating, and the solution is subjected to flash chromatography on 500 g of silica gel. Fractions 1 and 2, each eluted with 400 ml of trichloromethane/methanol (9:1), are discarded. Fractions 3-7, each eluted with 400 ml of the same mixture, are combined and concentrated by evaporation under 11 torr at 40°. The residue is stirred with diethyl ether, filtered off, and the yellow crystals are dried for 20 hours at 40°. The N-[4-(1-methyl-5-nitro-indol-3-yl-methyl)-3-methoxybenzoyl]-2-iodobenzenesulfonamide melts at 180°-230° (with decomposition). $^1$H-NMR (400 MHz, DMSO-d$_6$): 8.51 (d, 1H); 8.07 (d, d, 1H); 8.00 (d, d, 1H); 7.89 (d, d, 1H); 7.61 (d, 1H); 7.55 (d, 1H); 7.47 (d, d, 1H); 7.42 (t, d, 1H); 7.28 (s, 1H); 7.10 (d, 1H); 7.06 (t, d, 1H); 4.05 (s, 2H); 3.87 (s, 3H); 3.80 (s, 3H).

b) 20 mg of copper(I) iodide and 40 mg of bis(triphenylphosphine)palladium(II) dichloride are added at room temperature, with stirring, to a mixture of 1.21 g of N-[4-(1-methyl-5-nitro-indol-3-yl-methyl)-3-methoxybenzoyl]-2-iodobenzenesulfonamide, 0.8 g of a 60% solution of pent-4-yn-1-yl-methyl ether in ether/tetrahydrofuran (1:1) and 2.5 ml of triethylamine in 10.2 ml of dimethylformamide. The mixture is stirred for 15 hours at 70° in a small bomb tube and concentrated by evaporation under 0.1 torr at 40°. The residue is subjected to flash chromatography on 35 g of silica gel. Fractions 1-7, each eluted with 20 ml of ethyl acetate, are discarded. Fractions 8-17, each eluted with 20 ml of ethyl acetate, are combined and concentrated by evaporation under 11 torr at 40°. The residue, N-[4-(5-nitro-1-methyl-indol-3-yl-methyl)-3-methoxybenzoyl]-2-(5-methoxy-pent-1-yn-1-yl)-benzenesulfonamide, is in the form of a yellow powder. $^1$H-NMR (400 MHz, DMSO-d$_6$): 8.49 (d, 1H); 8.00 (d, d, 1H); 7.98 (m, b, 1H); 7.60 (d, 1H); 7.55 (d, 1H); 7.48 (d, d, 1H); 7.40 (m, b, 3H); 7.28 (s, 1H); 7.15 (d, b, 1H); 4.08 (s, 2H); 3.89 (s, 3H); 3.81 (s, 3H); 3.34 (t, 2H); 3.15 (s, 3H); 2.37 (t, 2H); 1.64 (m, 2H).

The N-[4-(5-nitro-1-methyl-indol-3-yl-methyl)-3-methoxybenzoyl]-2-(5-methoxy-pent-1-yn-1-yl)-benzenesulfonamide can alternatively be prepared as follows:

A solution of 2.18 g of 3-methoxy-4-(1-methyl-5-nitro-indol-3-yl-methyl)-benzoic acid N-succinimide ester, 1.40 g of 2-(5-methoxy-pent-1-yn-1-yl)-benzenesulfonamide and 2.3 ml of DBU in 50 ml of dichloromethane is stirred under argon for 15 hours at room temperature. The mixture is diluted with 50 ml of dichloromethane and washed twice with 20 ml of 1N hydrochloric acid each time, and with 20 ml of water, dried over magnesium sulfate and concentrated by evaporation under 11 torr at 40°. The residue is subjected to flash chromatography on 100 g of silica gel. Fractions 1 and 2, each eluted with 80 ml of ethyl acetate, are discarded. Fractions 3-7, eluted with the same solvent, are combined and concentrated by evaporation under 11 torr at 50°. The residue is stirred for 30 minutes with 50 ml of ether/petroleum ether (1:1), filtered, and the residue is dried for 15 hours under 0.1 torr at room temperature. The N-[4-(5-nitro-1-methyl-indol-3-yl-methyl)-3-methoxy-benzoyl]-2-(5-methoxy-pent-1-yn-1-yl)-benzenesulfonamide is in the form of a yellow powder.

c) 3.25 g of tin(II) chloride dihydrate are added with stirring to a suspension of 1.67 g of N-[4-(5-nitro-1-methyl-indol-3-yl-methyl)-3-methoxybenzoyl]-2-(5-methoxy-pent-1-yn-1-yl)-benzenesulfonamide in 60 ml of ethanol. The mixture is stirred under reflux for 15 hours, a solution forming. The solution is concentrated to dryness under 11 torr at 50°, and the residue is stirred with 20 ml of saturated aqueous sodium hydrogen carbonate solution and extracted twice with 50 ml of ethyl acetate each time. The combined organic phases are dried over magnesium sulfate and concentrated by evaporation under 11 torr at 50°. The residue is subjected to flash chromatography on 60 g of silica gel. Fractions 1-8, each eluted with 100 ml of ethyl acetate, are discarded. Fractions 9-25, each eluted with 100 ml of ethyl acetate/isopropanol (9:1), are combined and concentrated by evaporation under 11 torr at 50°. The residue, N-[4-(5-amino-1-methyl-indol-3-yl-methyl)-3-methoxybenzoyl]-2-(5-methoxy-pent-1-yn-1-yl)-benzenesulfonamide, is in the form of a yellow foam. $^1$H-NMR (100 MHz, DMSO-d$_6$): 7.91 (m, 1H); 7.53 (s, 1H); 7.32 (m, 3H); 7.07 (d, 1H); 6.93 (d, 1H); 6.80 (s, 1H); 6.60 (d, 1H); 6.54 (dd, 1H); 3.83 (s, 5H); 3.61 (s, 3H); 3.36 (t, 2H); 3.14 (s, 3H); 2.33 (t, 2H); 1.62 (m, 2H).

EXAMPLE 19

N-[4-[5-(Cyclopentyloxycarbonylamino)-1-methyl-indol-3-yl-methyl]-3-methoxybenzoyl]-2-(5-hydroxy-pent-1-yn-1-yl)-benzenesulfonamide 0.37 g of lithium hydroxide monohydrate and 10 ml of water are added to a solution of 1.2 g of N-[4-[5-(cyclopentyloxycarbonylamino)-1-methyl-indol-3-yl-methyl]-3-methoxybenzoyl]-2-(5-acetoxy-pent-1-yn-1-yl)-benzenesulfonamide in 40 ml of methanol/tetrahydrofuran=1/1. The mixture is stirred for 16 hours at room temperature, then the solvents are evaporated off at 15 torr and 40° and 50 ml of methylene chloride are added to the residue. Acidification is effected by adding 50 ml of 1N hydrochloric acid. The organic phase is separated off in a separating funnel. The aqueous phase is extracted twice with 20 ml of methylene chloride each time. The combined organic phases are washed with semi-saturated sodium chloride solution, dried over magnesium sulfate and concentrated by evaporation at 15 torr and 40°. The residue is chromatographed on 45 g of silica gel (Merck, ST 60, 4-63 μm) with 20% hexane in ethyl acetate to yield 1.1 g of the title compound in the form of a white amorphous solid. $^1$H-NMR (400 MHz, DMSO-$d_6$): 8.90 (s, b, 1H); 8.05 (m, 1H); 7.56 (m, 5H); 7.43 (d, d, 1H); 7.24 (d, 1H); 7.17 (d, d, 1H); 7.15 (d, 1H); 6.96 (s, 1H); 5.08 (m, 1H); 3.97 (s, 2H); 3.92 (s, 3H); 3.68 (s, 3H); 3.47 (t, 2H); 2.47 (t, 2H); 1.92–1.55 (m, 8H); 1.64 (m, 2H).

EXAMPLE 20

The following is prepared in a manner analogous to that described in Example 19:

N-[4-[5-(cyclopentyloxycarbonylamino)-1-methyl-indol-3-yl-methyl]-3-methoxybenzoyl]-2-(4-hydroxy-but-1-yn-1-yl)-benzenesulfonamide, white solid: $^1$H-NMR (400 MHz, DMSO-$d_6$): 8.75 (s, b, 1H); 8.01 (m, 1H); 7.59 (d, 1H); 7.57 (d, 1H); 7.42 (d, d, 1H); 7.40 (m, 3H); 7.22 (d, 1H); 3.94 (s, 2H); 3.88 (s, 3H); 3.67 (s, 3H); 3.60 (t, 2H); 2.50 (t, 2H); 1.91–1.55 (m, 8H); starting from N-[4-[5-(cyclopentyloxycarbonylamino)-1-methyl-indol-3-yl-methyl]-3-methoxybenzoyl]-2-(4-acetoxy-but-1-yn-1-yl)-benzenesulfonamide.

EXAMPLE 21

The following is prepared in a manner analogous to that described in Example 19:

N-[4-[5-(cyclopentyloxycarbonylamino)-1-methyl-indol-3-yl-methyl]-3-methoxybenzoyl]-2-(3-hydroxy-prop-1-yn-1-yl)-benzenesulfonamide, white amorphous solid: $^1$H-NMR (400 MHz, DMSO-$d_6$): 8.88 (b, 1H); 7.98 (m, b, 1H); 7.58 (d, 1H); 7.57 (d, 1H); 7.42 (d, d, 1H); 7.40 (m, 3H); 7.23 (d, 1H); 7.18 (d, d, 1H); 7.03 (d, b, 1H); 6.91 (s, 1H); 5.09 (m, 1H); 4.24 (s, 2H); 3.93 (s, 2H); 3.86 (s, 3H); 3.68 (s, 3H); 1.91–1.55 (m, 8H); starting from N-[4-[5-(cyclopentyloxycarbonylamino)-1-methyl-indol-3-yl-methyl]-3-methoxybenzoyl]-2-(3-acetoxy-prop-1-yn-1-yl)-benzenesulfonamide.

EXAMPLE 22

The following is prepared in a manner analogous to that described in Example 19:

N-[4-[5-(cyclopentyloxycarbonylamino)-1-methyl-indol-3-yl-methyl]-3-methoxybenzoyl]-2-(3-hydroxy-but-1-yn-1-yl)-benzenesulfonamide, white amorphous solid: $^1$H-NMR (400 MHz, DMSO-$d_6$): 8.88 (s, b, 1H); 8.07 (d, b, 1H); 7.58 (m, 5H); 7.43 (d, d, 1H); 7.24 (d, 1H); 7.17 (d, d, 1H); 7.13 (d, 1H); 6.95 (s, 1H); 5.08 (m, 1H); 4.61 (q, 1H); 3.96 (s, 2H); 3.91 (s, 3H); 3.68 (s, 3H); 1.91–1.55 (m, 8H); 1.31 (d, 3H); starting from 2-(3-acetoxy-but-1-yn-1-yl)-benzenesulfonamide (Example 11) by way of N-[4-[5-(cyclopentyloxycarbonylamino)-1-methyl-indol-3-yl-methyl]-3-methoxybenzoyl-2-(3-acetoxybut-1-yn-1-yl)-benzenesulfonamide.

EXAMPLE 23

The following is prepared in a manner analogous to that described in Example 19:

N-[4-[5-(cyclopentyloxycarbonylamino)-1-methyl-indol-3-yl-methyl]-3-methoxybenzoyl]-2-(4-hydroxy-pent-1-yn-1-yl)-benzenesulfonamide, white amorphous solid: $^1$H-NMR (400 MHz, DMSO-$d_6$): 8.76 (b, 1H); 8.02 (m, 1H); 7.58 (b, 2H); 7.45 (m, 3H); 7.42 (d, d, 1H); 7.22 (d, 1H); 7.08 (d, 1H); 6.92 (s, 1H); 5.09 (m, 1H); 3.95 (s, 2H); 3.90 (s, 3H); 3.88 (m, 2H); 3.68 (s, 3H); 2.44 (m, 2H); 1.91–1.55 (m, 8H); 1.14 (d, 3H); starting from N-[4-[5-(cyclopentyloxycarbonylamino)-1-methyl-indol-3-yl-methyl]-3-methoxybenzoyl]-2-(4-acetoxy-pent-1-yn-1-yl)-benzenesulfonamide.

EXAMPLE 24

N-[4-[5-(Cyclopentyloxycarbonylamino)-1-methyl-indol-3-yl-methyl]-3-methoxybenzoyl]-2-(3-acetoxy-3-methyl-but-1-yn-1-yl)-benzenesulfonamide 0.44 g of acetic anhydride and 0.1 g of 4-dimethylaminopyridine are added to a solution of 1.0 g of N-[4-[5-(cyclopentyloxycarbonylamino)-1-methyl-indol-3-yl-methyl]-3-methoxybenzoyl]-2-(3-hydroxy-3-methyl-but-1-yn-1-yl)-benzenesulfonamide in 6 ml of pyridine. The reaction solution is stirred for 20 hours at room temperature under argon. The reaction mixture is subsequently diluted with 100 ml of ethyl acetate. The ethyl acetate phase is washed twice with 80 ml of 1N hydrochloric acid each time, with 50 ml of water and with 50 ml of saturated sodium chloride solution. The ethyl acetate phase is dried over magnesium sulfate and concentrated by evaporation at 20 torr and 40°. The residue is chromatographed on 50 g of silica gel (Merck, ST 60, 40–63 μm) with hexane/ethyl acetate=1/1 to yield the title compound in the form of a white amorphous solid. $^1$H-NMR (400 MHz, DMSO-$d_6$): 8.87 (b, 1H); 8.06 (d, d, 1H); 7.61 (m, 3H); 7.55 (d, 1H); 7.50 (d, 1H); 7.41 (d, d, 1H); 7.22 (d, 1H); 7.14 (d, d, 1H); 7.13 (d, 1H); 6.94 (s, 1H); 5.06 (m, 1H); 3.95 (s, 2H); 3.90 (s, 3H); 3.66 (s, 3H); 1.91 (s, 3H); 1.89–1.52 (m, 8H); 1.61 (s, 6H).

EXAMPLE 25

N-[4-[5-(Cyclopentyloxycarbonylamino)-1-methyl-indol-3-yl-methyl]-3-methoxybenzoyl]-2-(pent-1-yn-1-yl)-benzenesulfonamide 1.07 g of 2-(pent-1-yn-1-yl)-benzenesulfonamide and 0.94 g of 3-[N-dimethylaminopropyl]-N-ethylcarbodiimide hydrochloride as well as 0.6 g of 4-dimethylaminopyridine are added to a solution of 2.0 g of 4-[5-(cyclopentyloxycarbonylamino)-1-methyl-indol-3-yl-methyl]-3-methoxy-benzoic acid in 50 ml of methylene chloride. The reaction mixture is stirred for 20 hours under argon and then diluted with 50 ml of methylene chloride. The methylene chloride phase is washed in a separating funnel twice with 1N hydrochloric acid and once with water. The methylene chloride phase is dried over magnesium sulfate and concentrated by evaporation at 20 torr and 40°. The residue is chromatographed on 80 g of silica gel (Merck Si60, 40–63 μm), ethyl acetate being used as eluant. The fractions containing the product are concentrated by evaporation at 20 torr and 40° to yield 2.2 g of the title compound in the form of a white amorphous solid. $^1$H-NMR (400 MHz, DMSO-$d_6$): 8.76 (s, b, 1H); 8.00 (d, 1H); 7.56 (m, 2H); 7.44 (m, 4H); 7.21 (d, 1H); 7.16 (d, d, 1H); 7.08 (d, 1H); 6.91 (s, 1H); 5.07 (m, 1H); 3.94 (s, 2H); 3.88 (s, 3H); 3.66 (s, 3H); 2.33 (t, 2H); 1.90–1.53 (m, 8H); 1.47 (m, 2H); 0.89 (t, 3H).

EXAMPLE 26

20 mg of copper(I) iodide, 40 mg of bis(triphenylphosphine)palladium(II) dichloride and 0.24 ml of 1-pentyne are added at room temperature, with stirring, to a suspension of 1.38 g of N-[4-[5-(cyclopentyloxycarbonylamino)-1-methyl-indol-3-yl-methyl]-3-methoxybenzoyl]-2-iodobenzenesulfonamide and 1.0 ml of triethylamine in 0.9 ml of dimethylformamide. The mixture is stirred for 15 hours at 70°, a further 0.4 ml of 1-pentyne is added, and stirring is continued for a further 4 hours at 70° C. The batch is cooled, 40 ml of ethyl acetate and 20 ml of water are added, the batch is shaken, the aqueous phase is removed and extracted with 10 ml of ethyl acetate, and the combined organic phases are washed with 20 ml of saturated sodium chloride solution. The organic phase is dried over magnesium sulfate and concentrated to dryness by evaporation under 11 torr at 40°. The residue is chromatographed on 100 g of silica gel. Fractions 1-3, each eluted with 60 ml of ethyl acetate, are discarded. Fractions 4-8, eluted with the same solvent, are combined and concentrated by evaporation under 11 torr at 40°. The residue is chromatographed again on 80 g of silica gel, elution again being carried out with ethyl acetate. The fractions containing the product are concentrated by evaporation under 11 torr at 40°. The N-[4-[5-(cyclopentyloxycarbonylamino)-1-methyl-indol-3-yl-methyl]-3-methoxybenzoyl]-2-(pent-1-yn-1-yl)-benzenesulfonamide is in the form of a beige powder.

$^1$H-NMR (400 MHz, DMSO-$d_6$): 8.76 (s, b, 1H); 8.00 (d, 1H); 7.56 (m, 2H); 7.44 (m, 4H); 7.21 (d, 1H); 7.16 (d, d, 1H); 7.08 (d, 1H); 6.91 (s, 1H); 5.07 (m, 1H); 3.94 (s, 2H); 3.88 (s, 3H); 3.66 (s, 3H); 2.33 (t, 2H); 1.90–1.53 (m, 8H); 1.47 (m, 2H); 0.89 (t, 3H).

The starting materials for this Example may be prepared as follows:

(a) A white solution of 1.0 g of 4-(1-methyl-5-nitro-indol-3-yl-methyl)-3-methoxy-benzoic acid in 50 ml of tetrahydrofuran is added dropwise, with stirring, to a solution of 0.79 g of 2-iodobenzenesulfonamide, 0.68 g of N-[3-dimethylaminopropyl]-N'-ethylcarbodiimide hydrochloride and 0.43 g of 4-dimethylaminopyridine in 30 ml of dichloromethane in an argon atmosphere. The mixture is stirred for 15 hours at room temperature. The precipitated yellow crystals are filtered off, subsequently washed with 40 ml of ether and chromatographed on 150 g of silica gel. Fraction 1, eluted with 80 ml of chloroform/methanol (9:1), is discarded. Fractions 2-7, eluted with the same solvent mixture, are combined and concentrated by evaporation under 11 torr at 40°. The residue is stirred with 30 ml of ether. The resulting suspension is filtered and the yellow crystals are dried for 20 hours under 0.3 torr at 40°. The N-[4-(1-methyl-5-nitro-indol-3-yl-methyl)-3-methoxybenzoyl]-2-iodobenzenesulfonamide melts at 179°–230° (decomposition).

(b) After the addition of 0.1 g of rhodium-on-carbon (5%) catalyst, a solution of 1.0 g of N-[4-(1-methyl-5-nitro-indol-3-yl-methyl)-3-methoxybenzoyl]-2-iodobenzenesulfonamide in 20 ml of tetrahydrofuran is hydrogenated for 4 hours at 20°–22° under normal pressure. A further 0.5 g of catalyst is added and hydrogenation is continued for a further 10 hours. The mixture is filtered through a glass fibre filter in order to remove the catalyst. Washing is carried out with 20 ml of tetrahydrofuran and the filtrate is concentrated to dryness under 11 torr at 40°. The residue is triturated with 30 ml of ether and the resulting suspension is filtered. The N-[4-(1-methyl-5-amino-indol-3-yl-methyl)-3-methoxybenzoyl]-2-iodobenzenesulfonamide is in the form of a beige powder. $^1$H-NMR (400 MHz, DMSO-$d_6$): 8.08 (d, d, 1H); 7.88 (d, d, 1H); 7.55 (d, 1H); 7.42 (t, d, 1H); 7.40 (d, d, 1H); 7.11 (d, 1H); 7.06 (t, d, 1H); 6.93 (d, 1H); 6.88 (s, 1H); 6.68 (d, 1H); 6.59 (d, d, 1H); 3.85 (s, 2H); 3.84 (s, 3H, —OCH$_3$); 6.36 (3, 3H, —NCH$_3$).

(c) A solution of 0.23 g of chloroformic acid cyclopentyl ester in 4 ml of dichloromethane is added, with stirring, to a suspension of 0.89 g of N-[4-(1-methyl-5-amino-indol-3-yl-methyl)-3-methoxybenzoyl]-2-iodobenzenesulfonamide and 0.5 ml of N-methylmorpholine in 6 ml of dichloromethane under argon. The brown solution is stirred for 2 hours at room temperature and poured onto 20 ml of 1N hydrochloric acid. The aqueous phase is removed and extracted twice with 10 ml of dichloromethane each time. The combined organic phases are washed with 10 ml of water, dried over magnesium sulfate, and concentrated by evaporation under 11 torr at 40°. The residue is subjected to flash chromatography on 90 g of silica gel. Fraction 1, eluted with 40 ml of ethyl acetate, is discarded. Fractions 2-4, each eluted with 40 ml of ethyl acetate, are combined and concentrated by evaporation under 11 torr at 40°. The residue is agitated with 10 ml of ethyl acetate/ether (1:2). The suspension is filtered and dried for 15 hours under 0.1 torr at 40°. The N-[4-[5-(cyclopentyloxycarbonylamino)-1-methyl-indol-3-yl-methyl]-3-methoxybenzoyl]-2-iodobenzenesulfonamide is in the form of beige crystals. M.p. 200°–220° with decomposition. $^1$H-NMR (400 MHz, DMSO-$d_6$): 8.75 (s, b, 1H); 8.09 (d, d, 1H); 7.91 (d, d, 1H); 7.60 (d, 1H); 7.57 (d, 1H); 7.44 (d, d, 1H); 7.41 (t, d, 1H); 7.20 (d, 1H); 7.17 (d, d, 1H); 7.06 (t, d, 1H); 7.02 (d, 1H); 6.90 (s, 1H); 5.08 (m, 1H); 3.92 (s, 2H); 3.85 (s, 3H); 3.66 (s, 3H); 1.90–1.5 (m, 8H).

EXAMPLE 27

The following may be prepared in a manner analogous to that described in one of the preceding Examples:

(a) N-[4-[5-(cyclopentyloxycarbonylamino)-1-methyl-indol-3-yl-methyl]-3-methoxybenzoyl]-2-(hex-1-yn-1-yl)-benzenesulfonamide;

(b) N-[4-[5-(cyclopentyloxycarbonylamino)-1-methyl-indol-3-yl-methyl]-3-methoxy-benzoyl]-2-(oct-1-yn-1-yl)-benzenesulfonamide; white solid; $^1$H-NMR (400 MHz, DMSO-$d_6$): 8.89 (s, 1H); 8.03 (d, 1H); 7.59 (d, 1H); 7.58 (d, 1H); 7.55–7.46 (m, 3H); 7.44 (dd, 1H); 7.23 (d, 1H); 7.12 (d, 1H); 7.08 (dd, 1H); 6.95 (s, 1H); 5.07 (m 1H); 3.95 (s, 2H); 3.92 (s, 3H); 3.68 (s, 3H); 2.39 (t, 2H); 1.92–1.17 (m, 14H); 0.82 (t, 3H);

(c) N-[4-[5-(cyclopentyloxycarbonylamino)-1-methyl-indol-3-yl-methyl]-3-methoxybenzoyl]-2-(2-cyclohexyl-ethynyl)-benzenesulfonamide;

(d) N-[4-[5-(cyclopentyloxycarbonylamino)-1-methyl-indol-3-yl-methyl]-3-methoxybenzoyl]-2-(2-cyclohex-1-enyl-ethynyl)-benzenesulfonamide; $^1$H-NMR (400 MHz, DMSO-$d_6$): 9.01 (s, b, 1H); 8.07 (m, 1H); 7.60 (m, 4H); 7.54 (d, 1H); 7.41 (dd, 1H); 7.12 (d, 1H); 6.99 (s, 1H); 6.19 (m, 1H); 5.07 (m, 1H); 3.95 (s, 2H); 3.91 (s, 3H); 3.68 (s, 3H); 2.07–1.47 (m, 16H).

(e) N-[4-[5-(cyclopentyloxycarbonylamino)-1-methyl-indol-3-yl-methyl]-3-methoxybenzoyl]-2-(3-hydroxy-3-methyl-pent-1-yn-1-yl)-benzenesulfonamide; $^1$H-NMR (400 MHz, DMSO-$d_6$): 8.89 (b, 1H); 7.99 (m, 1H); 7.58 (d, 1H); 7.57 (d, 1H); 7.44 (dd, 1H); 7.41 (m, 3H); 7.23 (d, 1H); 7.17 (dd, 1H); 7.04 (d, 1H); 6.90 (s, 1H); 5.08 (m, 1H); 3.93 (s, 2H); 3.87 (s, 3H); 3.67 (s, 3H); 1.92–1.54 (m, 8H); 1.59 (m, 2H); 1.35 (s, 3H); 0.93 (t, 3H).

(f) N-[4-[5-(cyclopentyloxycarbonylamino)-1-methyl-indol-3-yl-methyl[-3-methoxybenzoyl]-2-(3-acetoxy-3-methyl-pent-1-yn-1-yl)-benzenesulfonamide;

(g) N-[4-[5-(cyclopentyloxycarbonylamino)-1-methyl-indol-3-yl-methyl]-3-methoxy-benzoyl[-2-(3-hydroxy-3-ethyl-pent-1-yn-1-yl)-benzenesulfonamide; $^1$H-NMR (400 MHz, DMSO-$d_6$): 8.88 (b, 1H), 7.99 (m, 1H); 7.58 (d, 1H); 7.57 (d, 1H); 7.43 (dd, 1H); 7.41 (m, 3H); 7.22 (d, 1H); 7.17 (dd, 1H); 7.03 (d, b, 1H); 6.89 (s.

1H); 5.09 (m, 1H); 3.93 (s, 2H); 3.86 (s, 3H); 3.67 (s, 3H); 1.91–1.5 (m, 8H); 1.58 (m, 4H); 0.92 (t, 6H).

(h) N-[4-[5-(cyclopentyloxycarbonylamino)-1-methyl-indol-3-yl-methyl]-3-methoxybenzoyl]-2-(3-hydroxy-4-methyl-pent-1-yn-1-yl)-benzenesulfonamide; white powder; $^1$H-NMR (400 MHz, DMSO-$d_6$): 9.00 (s, b, 1H); 8.01 (d, b, 1H); 7.59 (b, 1H); 7.55 (d, 1H); 7.49 (m, b, 3H); 7.42 (dd, 1H); 7.24 (d, 1H); 7.16 (dd, 1H); 7.05 (d, b, 1H); 6.94 (s, 1H); 5.07 (m, 1H); 4.19 (d, b, 1H); 3.93 (s, 2H); 3.88 (s, 3H); 3.67 (s, 3H); 1.90–1.53 (m, 9H); 0.89 and 0.87 (2d, 6H);

(i) N-[4-[5-(cyclopentyloxycarbonylamino)-1-methyl-indol-3-yl-methyl]-3-methoxybenzoyl]-2-(3-acetoxy-4-methyl-pent-1-yn-1-yl)-benzenesulfonamide; white powder; $^1$H-NMR (400 MHz, DMSO-$d_6$): 8.99 (s, b, 1H); 8.06 (m, 1H); 7.63 (m, 3H); 7.57 (b, 1H); 7.52 (d, 1H); 7.41 (dd, 1H); 7.23 (d, 1H); 7.13 (dd, 1H); 6.98 (s, 1H); 5.42 (d, 1H); 5.05 (m, 1H); 3.90 (s, 3H); 3.84 (s, 2H); 3.66 (s, 3H); 1.97 (m, 1H); 1.95 (s, 3H); 3.66 (s, 3H); 1.97 (m, 1H); 1.95 (s, 3H); 1.90–1.50 (m, 8H); 0.89 and 0.84 (2d, 6H);

(j) N-[4-[5-(cyclopentyloxycarbonylamino)-1-methyl-indol-3-yl-methyl]-3-methoxybenzoyl]-2-[2-(1-hydroxy-cyclohexyl)-ethynyl]-benzenesulfonamide; white solid; $^1$H-NMR (400 MHz, DMSO-$d_6$): 8.88 (s, 1H); 8.05 (d, 1H); 7.65–7.50 (m, 5H); 7.42 (dd, 1H); 7.23 (d, 1H); 7.18 (d, d, 1H); 7.11 (d, 1H); 6.97 (s, 1H); 5.08 (m, 1H); 3.97 (s, 3H); 3.92 (s, 3H); 3.68 (s, 3H); 1.90–1.07 (m, 18H).

(k) N-[4-[5-(cyclopentyloxycarbonylamino)-1-methyl-indol-3-yl-methyl]-3-methoxybenzoyl]-[2-(1-hydroxy-cyclopentyl)-ethynyl]-benzenesulfonamide; white powder; $^1$H-NMR (400 MHz; DMSO-$d_6$): 8.85 (s, 1H); 7.97 (m, 1H); 7.58 (m, 2H); 7.42 (dd, 1H); 7.32 (s, b, 3H); 7.20 (d, 1H); 7.18 (dd, 1H); 6.99 (d, 1H); 6.84 (s, 1H); 5.05 (m, 1H); 3.90 (s, 3H); 3.82 (s, 3H); 3.63 (s, 3H); 1.98–1.50 (m, 16H); and (l) N-[4-[5-(cyclopentyloxycarbonylamino)-1-methyl-indol-3-yl-methyl]-3-methoxybenzoyl]-[2-(1-hydroxy-cyclopropyl)-ethynyl]-benzenesulfonamide.

EXAMPLES A TO H

Pharmaceutical Compositions.

The term "active ingredient" in the following indicates a compound I, in free form or in the form of a pharmaceutically acceptable salt, especially a compound that is described as a product in Examples 1 to 27, e.g. N-[4-[5-(cyclopentyloxycarbonylamino)-1-methyl-indol-3-yl-methyl]-3-methoxybenzoyl]-2-(5-methoxypent-1-yn-1-yl)-benzenesulfonamide.

EXAMPLE A

A propellant-containing, solid-aerosol-forming inhalation suspension, comprising 0.1% by weight of active ingredient.

| Composition | % by weight |
| --- | --- |
| active ingredient, micronised | 0.1 |
| sorbitan trioleate | 0.5 |
| propellant A (trichlorotrifluoroethane) | 4.4 |
| propellant B (dichlorodifluoromethane and 1,2-dichlorotetrafluoroethane) | 15.0<br>80.0 |

With the exclusion of moisture and using a customary homogenizer, the active ingredient is suspended, with the addition of the sorbitan trioleate, in the trichlorotrifluoroethane and the suspension is introduced into an aerosol container fitted with a metering valve. The container is sealed and filled with propellant B under pressure.

EXAMPLE B

An approximately 2% aqueous solution of the active ingredient in the form of its sodium or potassium salt, suitable for inhalation.

| Composition | |
| --- | --- |
| active ingredient (potassium or sodium salt) | 2000 mg |
| ethylenediaminetetraacetic acid disodium salt | 10 mg |
| benzalkonium chloride | 10 mg |
| water, freshly distilled | ad 100 ml |
| propellant | according to requirement |

The active ingredient is dissolved in approximately 60 ml of freshly distilled water and the stabiliser (ethylenediaminetetraacetic acid disodium salt) and the preservative (benzalkonium chloride) are added. After complete dissolution of all components, the resulting solution is made up to 100 ml and introduced into small pressure bottles. The bottles are sealed in a gas-tight manner. The propellant is added as required in gaseous from under pressure or in liquid form.

EXAMPLE C

An ointment, containing 0.05% by weight of active ingredient.

| Composition | % by weight |
| --- | --- |
| active ingredient | 0.05 |
| petroleum jelly | 45.00 |
| paraffin oil | 19.60 |
| cetyl alcohol | 5.00 |
| beeswax | 5.00 |
| sorbitan sesquioleate | 5.00 |
| p-hydroxybenzoic acid ester | 0.20 |
| water, demineralised | 20.15 |

The fatty substances and emulsifiers are melted together. The preservative is dissolved in water and the solution is emulsified into the fatty melt at elevated temperature. After cooling, a suspension of the active ingredient in a portion of the fatty melt is worked into the emulsion.

EXAMPLE D

Eyedrops, containing 0.3% by weight of active ingredient.

| Composition (10 000 10 ml bottles) | % by weight |
| --- | --- |
| active ingredient | 0.30 |
| disodium phosphate | 0.31 |
| citric acid | 0.15 |
| sodium chloride | 0.35 |
| sodium pyrosulfite | 0.10 |
| benzalkonium chloride | 0.01 |
| water, demineralised | 98.78 |

The active ingredient and all the additives indicated are stirred into 80 l of demineralised water under a nitrogen atmosphere. After complete dissolution of all the components, the solution is made up to 100 l with demineralised water, sterilised in an autoclave at 120° for 20 minutes and then filtered under sterile conditions through a membrane filter (pore diameter: 0.2 μm). A 10 ml portion of the filtrate is introduced under aseptic conditions into each bottle, which is fitted with a dropping pipette closure.

EXAMPLE E

Tablets each containing 50 mg of active ingredient.

| Composition (10 000 tablets) | |
|---|---|
| active ingredient | 500.0 g |
| lactose | 500.0 g |
| potato starch | 352.0 g |
| gelatin | 8.0 g |
| talcum | 60.0 g |
| magnesium stearate | 10.0 g |
| silicon dioxide (highly dispersed) | 20.0 g |
| ethanol | q.s. |

The active ingredient is mixed with the lactose and 292 g of the potato starch and the mixture is moistened with an ethanolic solution of the gelatin and granulated by means of a sieve. After drying, the granules are mixed with the remainder of the potato starch, the magnesium stearate, the talcum and the silicon dioxide and the mixture is compressed into 145 mg tablets each containing 50 mg of active ingredient which, if desired, may be provided with dividing notches for the purpose of finer adjustment of the dose.

EXAMPLE F

Film-coated tablets, each containing 100 mg of active ingredient.

| Composition (1000 film-coated tablets) | |
|---|---|
| active ingredient | 100.0 g |
| lactose | 100.0 g |
| corn starch | 70.0 g |
| talcum | 8.5 g |
| calcium stearate | 1.5 g |
| hydroxypropylmethylcellulose | 2.36 g |
| shellac | 0.64 g |
| water | q.s. |
| dichloromethane | q.s. |

The active ingredient, the lactose and 40 g of the corn starch are mixed together. The mixture is moistened with a paste prepared from 15 g of corn starch and water (with heating) and granulated. The granules are dried and the remainder of the corn starch, the talcum and the calcium stearate are mixed with the granules. The mixture is compressed into tablets (each weighing 280 mg) and these are film-coated with a solution of the hydroxypropylmethylcellulose and the shellac in dichloromethane (final weight of each film-coated tablet: 283 mg).

EXAMPLE G

Hard gelatin capsules, each containing 100 mg of active ingredient.

| Composition (1000 capsules) | |
|---|---|
| active ingredient | 100.0 g |
| lactose | 250.0 g |
| microcrystalline cellulose | 30.0 g |
| sodium lauryl sulfate | 2.0 g |
| magnesium stearate | 8.0 g |

The sodium lauryl sulfate is added to the lyophilised active ingredient through a sieve with a mesh size of 0.2 mm. The two components are homogeneously mixed. Then, first the lactose is added through a sieve with a mesh size of 0.6 mm and then the microcrystalline cellulose is added through a sieve with a mesh size of 0.9 mm. All four components are then homogeneously mixed for 10 minutes. Finally, the magnesium stearate is added through a sieve with a mesh size of 0.8 mm. After further mixing (3 minutes) a 390 mg portion of the resulting formulation is introduced into each size 0 hard gelatin capsule.

EXAMPLE H

An injection or infusion solution, containing 5 mg of active ingredient per 2.5 ml ampoule.

| Composition (1000 ampoules) | |
|---|---|
| active ingredient | 5.0 g |
| sodium chloride | 22.5 g |
| phosphate buffer solution (pH: 7.4) | 300.0 g |
| demineralised water | ad 2500.0 g |

The active ingredient and the sodium chloride are dissolved in 1000 ml of demineralised water. The solution is filtered through a microfilter. The phosphate buffer solution is added to the filtrate and the mixture is made up to 2500 ml with demineralised water. To prepare unit dose forms, a 2.5 ml portion of the mixture is introduced into each glass ampoule, which then contains 5 mg of active ingredient.

What is claimed is:

1. A compound of formula I

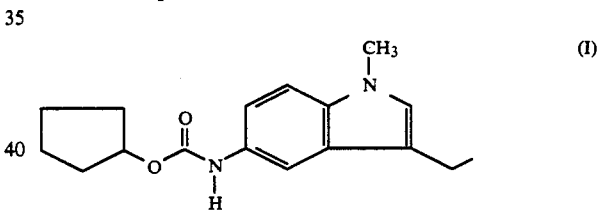

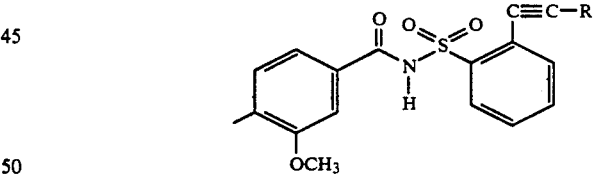

wherein

R is hydrogen or $C_1$-$C_7$alkyl, or wherein R is the structural element -alk-$R_1$ in which alk is $C_1$-$C_7$alkylene, $C_2$-$C_7$alkylidene or $C_3$-$C_6$cycloalkylidene and $R_1$ is hydroxy, $C_1$-$C_7$alkoxy, phenyl-$C_1$-$C_7$alkoxy or $C_2$-$C_7$alkanoyloxy;

in free form or in the form of a salt.

2. A compound according to claim 1 of formula I, wherein

R is hydrogen or $C_1$-$C_5$alkyl, or wherein R is the structural element -alk-$R_1$ in which alk is $C_1$-$C_5$alkylene, $C_2$-$C_7$alkylidene or $C_3$-$C_6$cycloalkylidene and $R_1$ is hydroxy, $C_1$-$C_4$alkoxy, phenyl-$C_1$-$C_4$alkoxy or $C_2$-$C_7$alkanoyloxy;

in free form or in the form of a salt.

3. A compound according to claim 1 of formula I, wherein

R is hydrogen or $C_1$-$C_4$alkyl, or wherein R is the structural element -alk-$R_1$ in which alk is $C_1$-$C_4$alkylene or $C_2$-$C_5$alkylidene and $R_1$ is hydroxy, $C_1$-$C_4$alkoxy or $C_2$-$C_5$alkanoyloxy;
in free form or in the form of a salt.

4. A compound according to claim 1 of formula I, wherein R is hydrogen or $C_1$-$C_3$alkyl; in free form or in the form of a salt.

5. A compound according to claim 1 of formula I, wherein
R is the structural element -alk-$R_1$ in which alk is $C_1$-$C_4$alkylene or $C_2$-$C_5$alkylidene and $R_1$ is hydroxy;
in free form or in the form of a salt.

6. A compound according to claim 1 of formula I, wherein
R is the structural element -alk-$R_1$ in which alk is 1,3-propylene, ethylidene or 2,2-propylidene and $R_1$ is hydroxy;
in free form or in the form of a salt.

7. N-[4-[5-(Cyclopentyloxycarbonylamino)-1-methyl-indol-3-yl-methyl]-3-methoxybenzoyl]-2-ethynyl-benzenesulfonamide according to claim 1 or a pharmaceutically acceptable salt thereof.

8. N-[4-[5-(Cyclopentyloxycarbonylamino)-1-methyl-indol-3-yl-methyl]-3-methoxybenzoyl]-2-(but-1-yn-1-yl)-benzenesulfonamide according to claim 1 or a pharmaceutically acceptable salt thereof.

9. N-[4-[5-(Cyclopentyloxycarbonylamino)-1-methyl-indol-3-yl-methyl]-3-methoxybenzoyl]-2-(3-methyl-but-1-yn-1-yl)-benzenesulfonamide according to claim 1 or a pharmaceutically acceptable salt thereof.

10. N-[4-[5-(Cyclopentyloxycarbonylamino)-1-methyl-indol-3-yl-methyl]-3-methoxybenzoyl]-2-(3-hyroxy-3-methyl-but-1-yn-1-yl)-benzenesulfonamide according to claim 1 or a pharmaceutically acceptable salt thereof.

11. N-[4-[5-(Cyclopentyloxycarbonylamino)-1-methyl-indol-3-yl-methyl]-3-methoxybenzoyl]-2-(5-hydroxy-pent-1-yn-1-yl)-benzenesulfonamide according to claim 1 or a pharmaceutically acceptable salt thereof.

12. A pharmaceutical composition comprising an effective leucotriene antagonistic amount of a compound of claim 1, or a pharmaceutically acceptable salt thereof, and at least one pharmaceutically acceptable carrier.

13. A pharmaceutical composition comprising an effective antiallergic amount of a compound of claim 1, or a pharmaceutically acceptable salt thereof, and at least one pharmaceutically acceptable carrier.

14. A pharmaceutical composition comprising an effective antiinflammatory amount of a compound of claim 1, or a pharmaceutically acceptable salt thereof, and at least one pharmaceutically acceptable carrier.

15. A method of treating an allergic condition in a warm blooded animal in need thereof comprising administering to said animal an effective antiallergic amount of a compound of claim 1 or a pharmaceutically acceptable salt thereof.

16. A method of treating an inflammatory condition in a warm blooded animal in need thereof comprising administering to said animal an effective antiinflammatory amount of a compound of claim 1 or a pharmaceutically acceptable salt thereof.

* * * * *